(12) United States Patent
Bolognia et al.

(10) Patent No.: US 11,647,678 B2
(45) Date of Patent: May 9, 2023

(54) COMPACT INTEGRATED DEVICE PACKAGES

(71) Applicant: Analog Devices International Unlimited Company, Limerick (IE)

(72) Inventors: David Frank Bolognia, Charlestown, MA (US); Christopher W. Hyde, Hollis, NH (US); Jochen Schmitt, Biedenkopf (DE); Vikram Venkatadri, Ayer, MA (US)

(73) Assignee: Analog Devices International Unlimited Company, Limerick (IE)

( * ) Notice: Subject to any disclaimer, the term of this patent is extended or adjusted under 35 U.S.C. 154(b) by 1601 days.

(21) Appl. No.: 15/681,904

(22) Filed: Aug. 21, 2017

(65) Prior Publication Data

US 2018/0062071 A1 Mar. 1, 2018

Related U.S. Application Data

(60) Provisional application No. 62/378,587, filed on Aug. 23, 2016.

(51) Int. Cl.
*H01L 43/02* (2006.01)
*H01L 43/08* (2006.01)
(Continued)

(52) U.S. Cl.
CPC ............ *H01L 43/02* (2013.01); *A61B 5/062* (2013.01); *A61B 5/063* (2013.01); *G01R 33/0047* (2013.01); *G01R 33/091* (2013.01); *H01L 23/3121* (2013.01); *H01L 23/5386* (2013.01); *H01L 23/5387* (2013.01); *H01L 25/04* (2013.01); *H01L 25/16* (2013.01);
(Continued)

(58) Field of Classification Search
CPC .................... H01L 23/5386; H01L 23/5387
See application file for complete search history.

(56) References Cited

U.S. PATENT DOCUMENTS 3,724,274 A 4/1973 Millar
3,949,274 A 4/1976 Anacker
(Continued)

FOREIGN PATENT DOCUMENTS

CN 102129053 7/2011
CN 202393897 8/2012
(Continued)

OTHER PUBLICATIONS

Li, "Polymer Flip-chip Bonding of Pressure Sensors on Flexible Kapton Film for Neonatal Catheters", A thesis submitted to the Division of Research and Advanced Studies of the University of Cincinnati (2004).
(Continued)

*Primary Examiner* — Omar F Mojaddedi
(74) *Attorney, Agent, or Firm* — Knobbe, Martens, Olson & Bear, LLP

(57) ABSTRACT

An integrated device package sized and shaped to fit in a small space, such as within a body lumen or cavity of a human patient, is disclosed. The integrated device package includes a package substrate and integrated device dies. The first and second integrated device dies are angled relative to one another about the longitudinal axis by a fixed non-parallel angle.

15 Claims, 13 Drawing Sheets

(51) Int. Cl.
*H01L 25/16* (2006.01)
*H01L 25/04* (2014.01)
*H01L 23/538* (2006.01)
*H01L 23/31* (2006.01)
*H01L 23/13* (2006.01)
*A61B 5/06* (2006.01)
*G01R 33/00* (2006.01)
*G01R 33/09* (2006.01)
*A61B 34/20* (2016.01)
*A61B 90/00* (2016.01)
*A61B 17/00* (2006.01)
*A61B 5/00* (2006.01)

(52) U.S. Cl.
CPC ............ *H01L 43/08* (2013.01); *A61B 5/6852* (2013.01); *A61B 2017/00526* (2013.01); *A61B 2034/2048* (2016.02); *A61B 2034/2051* (2016.02); *A61B 2090/064* (2016.02); *A61B 2090/397* (2016.02)

(56) References Cited

U.S. PATENT DOCUMENTS

| | | | |
|---|---|---|---|
| 4,006,394 A | 2/1977 | Cuda | |
| 4,742,183 A | 5/1988 | Soloway et al. | |
| 4,928,206 A | 5/1990 | Porter et al. | |
| 5,074,863 A | 12/1991 | Dines | |
| 5,126,286 A | 6/1992 | Chance | |
| 5,289,122 A | 2/1994 | Shigeno | |
| 5,405,337 A | 4/1995 | Maynard | |
| 5,452,182 A | 9/1995 | Eichelberger et al. | |
| 5,554,806 A | 9/1996 | Mizuno et al. | |
| 5,555,159 A | 9/1996 | Dore | |
| 5,616,863 A | 4/1997 | Koen | |
| 5,644,230 A * | 7/1997 | Pant | G01R 33/0206 174/254 |
| 5,731,222 A | 3/1998 | Malloy et al. | |
| 5,833,608 A | 11/1998 | Acker | |
| 5,903,440 A | 5/1999 | Blazier et al. | |
| 6,040,624 A | 3/2000 | Chambers et al. | |
| 6,052,610 A | 4/2000 | Koch | |
| 6,075,708 A | 6/2000 | Nakamura | |
| 6,078,102 A | 6/2000 | Crane, Jr. et al. | |
| 6,097,183 A | 8/2000 | Goetz | |
| 6,106,476 A | 8/2000 | Corl et al. | |
| 6,169,254 B1 | 1/2001 | Pant et al. | |
| 6,184,680 B1 | 2/2001 | Shinoura et al. | |
| 6,225,688 B1 | 5/2001 | Kim et al. | |
| 6,278,271 B1 | 8/2001 | Schott | |
| 6,291,894 B1 | 9/2001 | Farnworth et al. | |
| 6,304,082 B1 | 10/2001 | Gualtieri et al. | |
| 6,326,908 B1 | 12/2001 | Hoffman et al. | |
| 6,339,191 B1 | 1/2002 | Crane, Jr. et al. | |
| 6,348,427 B1 | 2/2002 | Hamada et al. | |
| 6,511,863 B2 | 1/2003 | Farnworth et al. | |
| 6,536,123 B2 | 3/2003 | Tamura | |
| 6,570,246 B1 | 5/2003 | Lee et al. | |
| 6,591,492 B2 | 7/2003 | Farrar | |
| 6,705,005 B2 | 3/2004 | Blazier et al. | |
| 6,721,189 B1 | 4/2004 | Haba | |
| 6,777,261 B2 | 8/2004 | Farnworth et al. | |
| 6,784,659 B2 | 8/2004 | Haji-Sheikh | |
| 6,852,607 B2 | 2/2005 | Song et al. | |
| 6,903,465 B2 | 6/2005 | Farnworth et al. | |
| 6,993,443 B2 | 1/2006 | Harle | |
| 6,993,974 B2 | 2/2006 | Tenerz et al. | |
| 7,012,812 B2 | 3/2006 | Haba | |
| 7,115,984 B2 | 10/2006 | Poo et al. | |
| 7,202,552 B2 | 4/2007 | Zhe et al. | |
| 7,211,886 B2 | 5/2007 | Hsu et al. | |
| 7,265,719 B1 | 9/2007 | Moosbrugger et al. | |
| 7,301,332 B2 | 11/2007 | Govari et al. | |
| 7,307,415 B2 | 12/2007 | Seger et al. | |
| 7,375,009 B2 | 5/2008 | Chua et al. | |
| 7,408,342 B2 | 8/2008 | Desplats | |
| 7,408,343 B2 | 8/2008 | Dmytriw | |
| 7,420,262 B2 | 9/2008 | Bauer et al. | |
| 7,429,788 B2 | 9/2008 | Clayton et al. | |
| 7,467,552 B2 | 12/2008 | MacGugan | |
| 7,525,309 B2 | 4/2009 | Sherman et al. | |
| 7,812,596 B2 | 10/2010 | Potter et al. | |
| 7,839,657 B2 | 11/2010 | Nodine | |
| 8,018,223 B2 | 9/2011 | Latoria | |
| 8,115,480 B2 | 2/2012 | Masubuchi | |
| 8,134,361 B2 | 3/2012 | Azumi et al. | |
| 8,148,978 B2 | 4/2012 | Sherman et al. | |
| 8,421,453 B2 | 4/2013 | Bauer | |
| 8,692,366 B2 | 4/2014 | Xue et al. | |
| 8,750,961 B1 | 6/2014 | Ries | |
| 8,786,278 B2 | 7/2014 | Ohta | |
| 8,836,132 B2 | 9/2014 | Xue | |
| 8,957,679 B2 | 2/2015 | Loreit et al. | |
| 9,000,763 B2 | 4/2015 | Ausserlechner | |
| 9,030,194 B2 | 5/2015 | Dolsak | |
| 9,069,033 B2 | 6/2015 | Chen et al. | |
| 9,093,360 B2 | 7/2015 | Bolognia | |
| 9,103,657 B2 | 8/2015 | Ruigrok | |
| 9,116,022 B2 | 8/2015 | Bolognia | |
| 9,234,736 B2 | 1/2016 | Engel et al. | |
| 9,268,001 B2 | 2/2016 | Ausserlechner | |
| 9,278,851 B2 | 3/2016 | Xue | |
| 9,286,924 B1 | 3/2016 | Akatsuka et al. | |
| 9,297,863 B2 | 3/2016 | Jeng et al. | |
| 9,332,940 B2 | 5/2016 | Bolognia | |
| 9,335,149 B2 | 5/2016 | Stark | |
| 9,372,064 B2 | 6/2016 | Zwijze et al. | |
| 9,470,552 B2 | 10/2016 | Ausserlechner | |
| 9,475,694 B2 | 10/2016 | Martizon, Jr. et al. | |
| 9,494,661 B2 | 11/2016 | Paul et al. | |
| 9,513,344 B2 | 12/2016 | Ausserlechner | |
| 9,601,455 B2 | 3/2017 | Nishiyama et al. | |
| 9,624,095 B2 | 4/2017 | Millett et al. | |
| 9,625,276 B2 | 4/2017 | Ausserlechner | |
| 9,658,298 B2 | 5/2017 | Cai et al. | |
| 9,780,471 B2 | 10/2017 | Van Rijswijk | |
| 9,877,660 B2 | 1/2018 | O'Connell et al. | |
| 9,895,053 B2 | 2/2018 | Fujimori et al. | |
| 9,941,237 B2 | 4/2018 | Nishiyama et al. | |
| 9,995,600 B2 | 6/2018 | Nagarkar | |
| 10,081,266 B2 | 9/2018 | Draeger | |
| 10,201,311 B2 | 2/2019 | Chou et al. | |
| 10,281,710 B2 | 5/2019 | Fujimori | |
| 10,337,888 B2 | 7/2019 | Jost et al. | |
| 2002/0005715 A1 | 1/2002 | Sato | |
| 2002/0077752 A1 | 6/2002 | Burreson et al. | |
| 2002/0180605 A1 | 12/2002 | Ozguz et al. | |
| 2003/0120150 A1 | 6/2003 | Govari | |
| 2003/0146332 A1 | 8/2003 | Vinding | |
| 2003/0209789 A1 | 11/2003 | Hanson et al. | |
| 2004/0157410 A1 | 8/2004 | Yamaguchi | |
| 2004/0169244 A1 | 9/2004 | MacGugan | |
| 2005/0184187 A1 | 8/2005 | Ullman et al. | |
| 2005/0230795 A1 | 10/2005 | Furuyama et al. | |
| 2006/0082363 A1 | 4/2006 | Ricks | |
| 2006/0129061 A1 | 6/2006 | Kaneto et al. | |
| 2006/0151864 A1 | 7/2006 | Anderson et al. | |
| 2006/0261453 A1 | 11/2006 | Lee et al. | |
| 2007/0035294 A1 | 2/2007 | Peczalski | |
| 2007/0053504 A1 | 3/2007 | Sato et al. | |
| 2008/0052932 A1* | 3/2008 | Xue | G01C 17/28 33/356 |
| 2008/0175425 A1 | 7/2008 | Roberts et al. | |
| 2008/0285111 A1 | 11/2008 | Ishii et al. | |
| 2009/0027048 A1 | 1/2009 | Sato | |
| 2009/0121342 A1 | 5/2009 | Minakawa et al. | |
| 2009/0243402 A1 | 10/2009 | O'Day | |
| 2009/0268019 A1 | 10/2009 | Ishii et al. | |
| 2009/0295381 A1 | 12/2009 | Theuss | |
| 2009/0315554 A1 | 12/2009 | Witcraft et al. | |
| 2010/0072992 A1 | 3/2010 | Bauer | |
| 2010/0078739 A1 | 4/2010 | Xue et al. | |
| 2010/0090295 A1 | 4/2010 | Zhe et al. | |
| 2010/0130923 A1 | 5/2010 | Cleary et al. | |

(56) References Cited

U.S. PATENT DOCUMENTS

| | | |
|---|---|---|
| 2010/0155863 A1 | 6/2010 | Weekamp |
| 2010/0197148 A1 | 8/2010 | Rudisill et al. |
| 2010/0331635 A1 | 12/2010 | Wang |
| 2011/0018143 A1 | 1/2011 | Chua et al. |
| 2011/0074406 A1 | 3/2011 | Mather |
| 2011/0132643 A1* | 6/2011 | Hattori ............... H05K 1/09 174/254 |
| 2011/0147921 A1* | 6/2011 | Mohammed ........... H01L 23/04 438/117 |
| 2011/0149522 A1 | 6/2011 | Johann et al. |
| 2011/0227569 A1 | 9/2011 | Cai et al. |
| 2011/0234218 A1 | 9/2011 | Lagouge |
| 2011/0248706 A1 | 10/2011 | Davis |
| 2012/0217960 A1 | 8/2012 | Ausserlechner |
| 2012/0256619 A1 | 10/2012 | Muto et al. |
| 2012/0268113 A1 | 10/2012 | Sato |
| 2013/0023769 A1 | 1/2013 | Tsai et al. |
| 2013/0134969 A1 | 5/2013 | Ohta |
| 2013/0249542 A1 | 9/2013 | Zhao |
| 2013/0313130 A1 | 11/2013 | Little et al. |
| 2013/0320969 A1 | 12/2013 | Reichenbach |
| 2013/0335072 A1 | 12/2013 | Malzfeldt |
| 2014/0005521 A1 | 1/2014 | Kohler et al. |
| 2014/0197531 A1* | 7/2014 | Bolognia ............... H01L 25/18 257/723 |
| 2014/0266187 A1 | 9/2014 | Mather |
| 2015/0066007 A1 | 3/2015 | Srivastava |
| 2015/0084619 A1 | 3/2015 | Stark |
| 2015/0164469 A1 | 6/2015 | Corl |
| 2015/0204950 A1 | 7/2015 | Ausserlechner |
| 2015/0285611 A1 | 10/2015 | Lowery |
| 2016/0056091 A1* | 2/2016 | Kim ............... H01L 23/3121 257/368 |
| 2016/0161288 A1 | 6/2016 | Lu |
| 2016/0169985 A1 | 6/2016 | Weber |
| 2016/0178397 A1 | 6/2016 | Jost et al. |
| 2016/0249817 A1 | 9/2016 | Mazar et al. |
| 2016/0327618 A1* | 11/2016 | Yuan ...................... G01C 17/28 |
| 2017/0014198 A1 | 1/2017 | Gravlee |
| 2017/0108354 A1 | 4/2017 | Maiterth |
| 2017/0136906 A1 | 5/2017 | Draeger |
| 2017/0164867 A1 | 6/2017 | Kassab et al. |
| 2017/0276738 A1 | 9/2017 | Holm |
| 2017/0356764 A1 | 12/2017 | Deak et al. |
| 2018/0021545 A1 | 1/2018 | Mitchell et al. |
| 2018/0042518 A1* | 2/2018 | Fruci ...................... A61B 5/287 |
| 2018/0062071 A1 | 3/2018 | Bolognia et al. |
| 2018/0113176 A1 | 4/2018 | Nagata |
| 2018/0122784 A1 | 5/2018 | Bolognia |
| 2018/0128648 A1 | 5/2018 | Schmitt |
| 2018/0216967 A1 | 8/2018 | Sun |
| 2018/0274896 A1 | 9/2018 | Anagawa |

FOREIGN PATENT DOCUMENTS

| | | |
|---|---|---|
| CN | 202604785 U | 12/2012 |
| CN | 103038782 A | 4/2013 |
| CN | 103403627 A | 11/2013 |
| CN | 103622688 A | 3/2014 |
| CN | 103720461 A | 4/2014 |
| CN | 103826528 A | 5/2014 |
| CN | 103889308 A | 6/2014 |
| CN | 105452812 | 3/2016 |
| DE | 10 2011 001 422 A1 | 9/2012 |
| DE | 102017125732 A1 | 5/2018 |
| EP | 0575800 A2 | 12/1993 |
| EP | 0 575 800 A3 | 10/1996 |
| EP | 0 783 666 B1 | 6/1999 |
| EP | 1 321 743 | 6/2003 |
| EP | 1365208 A1 | 11/2003 |
| GB | 2528251 A | 1/2016 |
| JP | 09121015 A | 5/1997 |
| JP | 2002-022403 A | 1/2002 |
| JP | 2002-529133 A | 9/2002 |
| JP | 2008-305395 A | 12/2008 |
| JP | 2009-289724 A | 12/2009 |
| JP | 2010-258038 | 11/2010 |
| JP | 2011-501163 A | 1/2011 |
| JP | 2011-220977 A | 11/2011 |
| JP | 2016-169685 A | 9/2016 |
| JP | 2018-072344 A | 5/2018 |
| WO | WO 96/10731 | 4/1996 |
| WO | WO 00/27281 | 5/2000 |
| WO | WO 01/04656 | 1/2001 |
| WO | WO 2002/052221 | 12/2001 |
| WO | WO 2009/052537 | 4/2009 |
| WO | WO 2011/080935 | 7/2011 |
| WO | WO 2016/020326 | 2/2016 |
| WO | WO 2016/127130 A1 | 8/2016 |
| WO | WO 2016/171597 A1 | 10/2016 |

OTHER PUBLICATIONS

Office Action in Chinese Patent Application No. 201710726748.3 dated May 11, 2020.

Office Action in Chinese Patent Application No. 201710726748.3 dated Oct. 12, 2020.

Tanase et al., "Multi-parameter sensor system with intravascular navigation for catheter/guide wire application", Sensors and Actuators A 97-98:116-124 (2002).

Images obtained on Jun. 13, 2011 from a web search related to three-dimensional packaging.

Sensors—HARTING Mitronics, HARTING Pushing Performance, in 2 pages (downloaded from World Wide Web page: harting-mitronics.ch/en/produkte/anwendungen/sensorik/index.php on Jul. 11, 2011).

Office Action issued in Chinese application No. 201710726748.3 dated Sep. 24, 2019.

* cited by examiner

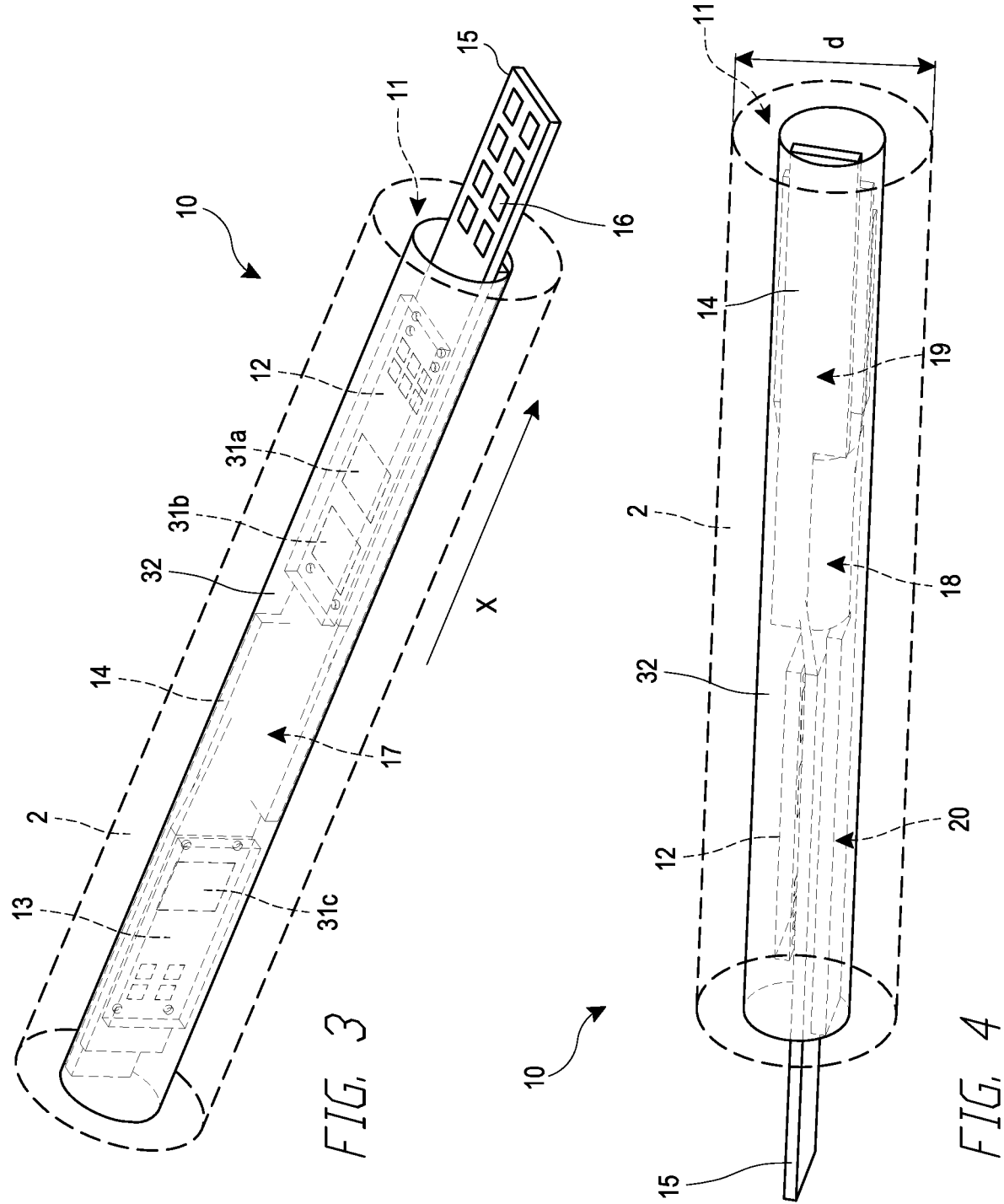

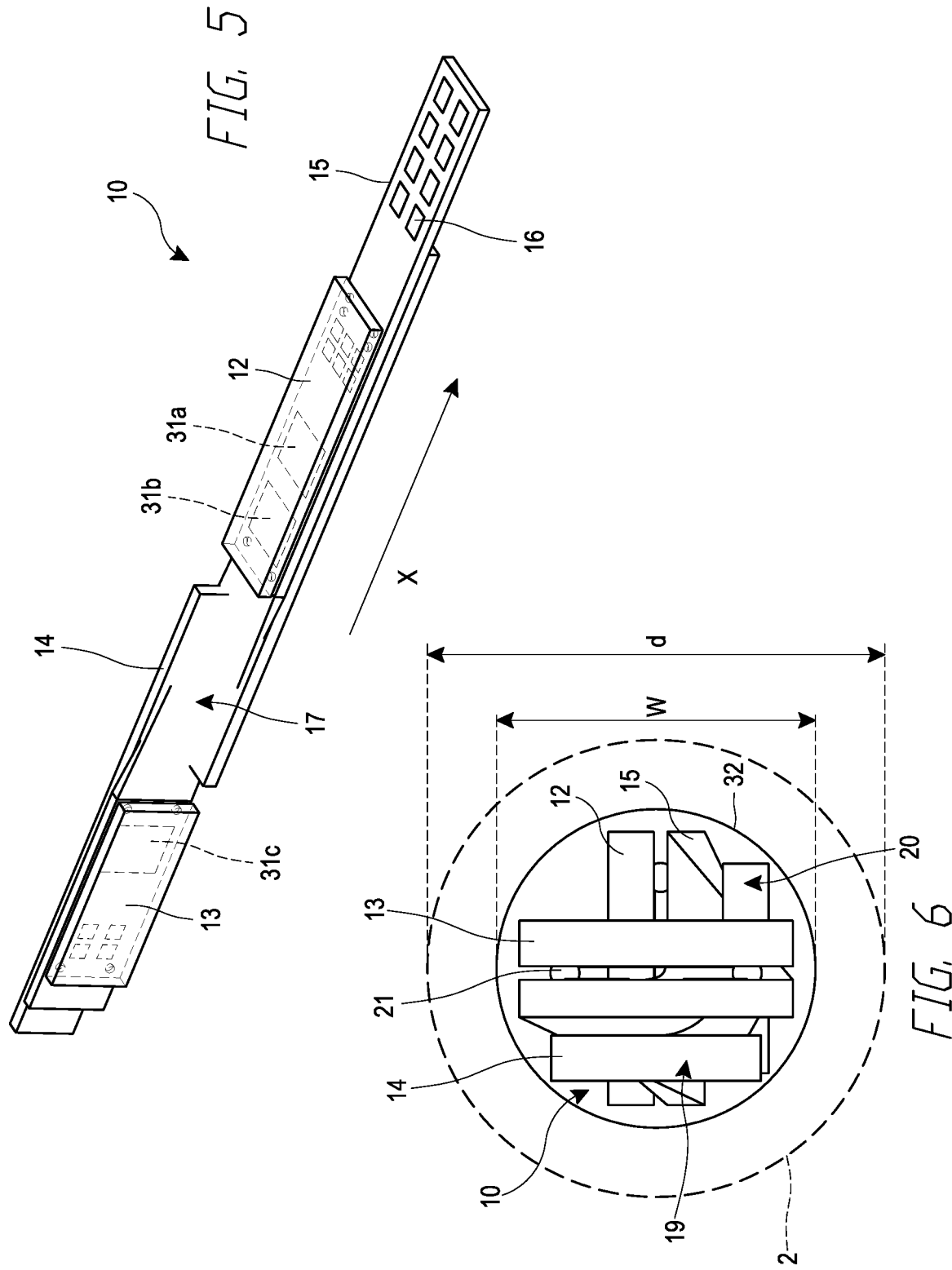

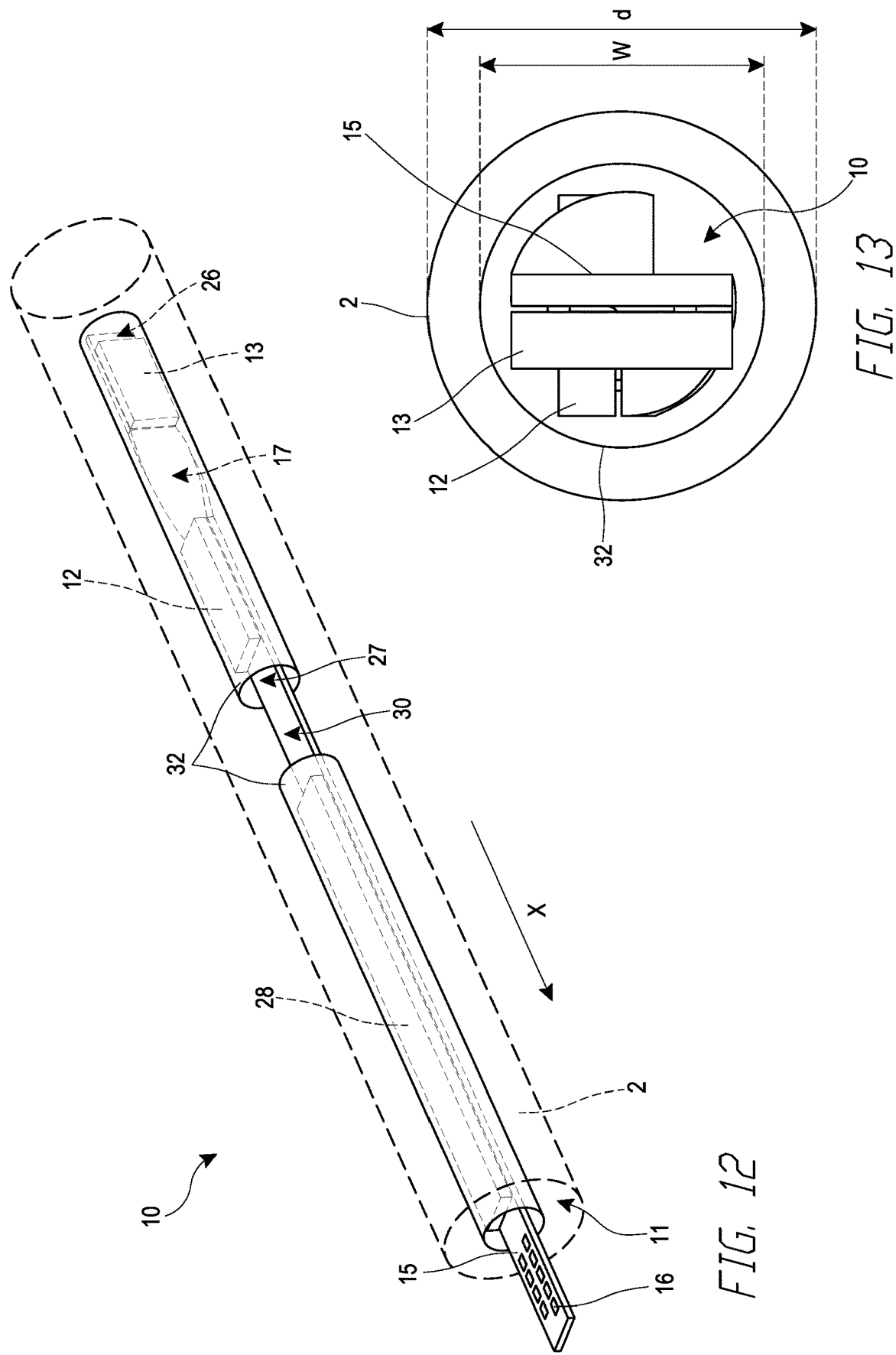

COMPACT INTEGRATED DEVICE PACKAGES

CROSS-REFERENCE TO RELATED APPLICATIONS

This application claims the benefit of U.S. Provisional Application No. 62/378,587, entitled "COMPACT INTEGRATED DEVICE PACKAGES," filed Aug. 23, 2016, the entire disclosure of which is incorporated herein by reference for all purposes.

BACKGROUND

Field

The field relates to compact integrated device packages, and, in particular, to compact position sensor packages (e.g., magnetic sensors) sized and shaped to fit in a small space, such as within a body lumen, a hollow guidewire, a catheter lumen, minimally invasive surgical or diagnostic instrument or a cavity of a human patient.

Description of the Related Art

Many medical devices utilize a catheter or other elongate structure to access internal organs of a human patient. For example, in various treatment and diagnostic procedures, a clinician can insert a guidewire through a body lumen of the patient and can deliver a distal end of the guidewire to a location within the patient. In cardiac treatment procedures, such as stent delivery, percutaneous transluminal angioplasty, cardiac mapping and ablation, cardiac pumping, or other percutaneous procedures, the clinician can use the Seldinger technique to access the patient's vascular system (e.g., the femoral artery) for insertion of the guidewire. Once the guidewire is placed at the target location, the clinician can insert a catheter system or other elongate structure over the guidewire to guide the catheter system to the treatment site.

Since the treatment or diagnosis site may be remote from the insertion site, it can be challenging to monitor the location and/or orientation of the distal end of the guidewire and/or the working end of the catheter system. The small diameter of the patient's blood vessels can limit the maximum diameter of the catheter system, which in turn makes it challenging to incorporate sensor device dies and associated packaging structures. Moreover, since the sensor device dies and other electronics may dissipate power and may be used in the human body, it can be important to provide a device package that does not generate significant heat, particularly as a point source, but rather spreads the heat over more area, to lower point temperatures. Similarly, the skilled artisan will recognize other applications in which very small tools or devices should be located with precision.

Accordingly, there remains a continuing need for improved compact integrated device packages for sensing the location of small tools or devices, such as medical devices.

SUMMARY OF THE INVENTION

Specific implementations will now be described with reference to the following drawings, which are provided by way of example, and not limitation.

In one aspect, an integrated device package is disclosed. The package includes a package substrate, a first integrated device die mounted to the substrate, a second integrated device die also mounted to the substrate, and a molding material. The first and second device dies are longitudinally spaced from each other and the dies are angled relative to one another about the longitudinal axis by a fixed non-parallel angle. The molding compound is disposed over the package substrate at least partially between the dies to maintain the fixed non-parallel angle.

In some embodiments, the first and second device dies are sensor dies. The sensor dies can include magnetoresistance sensors, such as, for example, anisotropic magnetoresistance (AMR) sensors, tunneling magnetoresistance (TMR) sensors, and giant magnetoresistance (GMR) sensors. The first integrated device die can be configured to sense a position of the package along first and second orthogonal axes. The second integrated device die can be configured to sense the position of the package along a third axis orthogonal to the first and second axes. A third integrated device die can be mounted to the package substrate and can be configured to process data, such as the transduced magnetic flux intensity and position information by the first and second integrated device dies. The third integrated device die can be an amplifier, and/or analog-to-digital converter (ADC) or other signal conditioning circuitry.

In some embodiments, one or more of the first and second integrated device dies can be flip chip mounted, or wire bonded to the package substrate.

In some embodiments, the integrated device package along the longitudinal axis can be in a range of 3 mm to 15 mm. In some embodiments, the package can have a width along a transverse axis that is perpendicular to the longitudinal axis, and the width can be in a range of 50 microns to 600 microns.

In some embodiments, the fixed non-parallel angle can be formed by a twisted section. The twisted section can be embedded in the molding material. The fixed non-parallel angle can be in a range of 89° to 91°.

In some embodiments, the molding material can be disposed over the first and second integrated device dies.

In some embodiments, the package can further include a bracket assembly extending along a longitudinal axis configured to provide stiffness for the first and second integrated device dies. In some embodiments, the bracket assembly can comprise a plurality of brackets that are separated from one another. In some embodiments, the bracket materials are made with materials with low magnetic susceptibility.

In another aspect, another integrated device package is disclosed. The package included a package substrate, a first integrated device die mounted to the substrate, a second integrated device die also mounted to the substrate, and a molding material. The first and second device dies are longitudinally spaced from each other and the dies are angled relative to one another about the longitudinal axis by a fixed non-parallel angle. The package has a width along a transverse axis that is perpendicular to the longitudinal axis, the width being in a range of 50 microns to 600 microns.

In some embodiments, the package can further include a molding material that fixes the fixed non-parallel angle.

In some embodiments, the first and second dies can be sensor dies. The sensor dies can include magnetoresistance sensors, such as, for example, anisotropic magnetoresistance (AMR) sensors, tunneling magnetoresistance (TMR) sensors, and giant magnetoresistance (GMR) sensors.

In another aspect, a method for manufacturing an integrated device package is disclosed. The method includes mounting a first integrated die and a second integrated device die on a package substrate. The first integrated device die is longitudinally spaced from the second integrated device die. The method further includes deforming the package substrate so as to make the first and second integrated device dies angled relative to one another about the longitudinal axis by a fixed non-parallel angle.

In some embodiments, the method can further include applying a molding material at least to a portion of the package substrate to maintain the fixed non-parallel angle by a molding material.

In some embodiments, the first and second integrated device dies comprise sensor dies.

In some embodiments, the deforming the package substrate can include offsetting the first and second dies in a transverse axis, twisting the package substrate, and/or adhering the package substrate to a bracket assembly.

In another aspect, another integrated device package is disclosed. The package included an elongate bracket extending along a longitudinal axis that has a first support and second support surfaces. The surfaces are placed at a fixed non-parallel angle about the longitudinal axis relative to the first support surface. The package also includes a package substrate comprising a first portion and a second portion. The first portion is mechanically connected to the first support surface. The second portion is mechanically connected to the second support surface. The package also includes a first integrated device die and a second integrated device die that are mounted to the first portion and the second portion respectively. The package transverse dimension is less than 600 microns, where the transverse dimension is a dimension transverse to the longitudinal axis.

In some embodiments, the first portion and the second portion form part of a single package and/or are defined by separate package substrates.

In some embodiments, the first integrated device die can be spaced from the second integrated device die along the longitudinal axis.

In some embodiments, the package substrate can comprise one or more bends. The bends can comprise a twisted section. The twisted section is placed between the first and second portions so as to position the first and second portions at the fixed non-parallel angle relative to one another.

In some embodiments, the first and second integrated device dies are sensor dies. The sensor dies may be magnetoresistance sensors. For examples, the magnetoresistance sensors may be anisotropic magnetoresistance (AMR) sensors, tunneling magnetoresistance (TMR) sensors, and giant magnetoresistance (GMR) sensors. The first integrated device die can be configured to sense a position of the package along first and second orthogonal axes and the second integrated device die can be configured to sense the position of the package along a third axis orthogonal to the first and second axes.

In some embodiments, the package can also include a third integrated device die mounted to the package substrate that can be configured to process position data transduced by the first and second integrated device dies.

In some embodiments, the bracket can include a transverse portion placed between and connecting the first and second support surfaces.

In some embodiments, one or more of the first and second integrated device dies can be flip chip mounted to and/or wire bonded to the package substrate.

In some embodiments, a length of the bracket along the longitudinal axis can be in a range of 1 mm to 8 mm, 1 mm to 6 mm, 2 mm to 6 mm, or 3 mm to 5 mm.

In some embodiments, the package can have a width along a transverse axis that is perpendicular to the longitudinal axis, the width being in a range of 50 microns to 600 microns, 100 microns to 450 microns, or 100 microns to 400 microns.

In some embodiments, the fixed non-parallel angle is in a range of 89° to 91° or 89.5° to 90.5°.

In some embodiments, the package substrate can be adhered to the bracket. In some embodiments, the package substrate can extend beyond the bracket along the longitudinal axis.

In some embodiments, the bracket can be a non-magnetic material. In some embodiments, the bracket can be copper.

In some embodiments, the package can also include a package body in which the first and second integrated device dies are disposed.

In some embodiments, the elongate bracket can comprise a first bracket component having the first support surface and a second bracket component having the second support surface, where the first and second bracket components are separated by the package substrate along a longitudinal axis.

In some embodiments, the package can further comprise a molding material that fixes the fixed non-parallel angle.

In another aspect, another integrated package is disclosed. The integrated package includes a package substrate, a first magnetic sensor die mounted to the package substrate, and a second magnetic sensor die mounted to the package substrate. The first magnetic sensor die is spaced from the second magnetic sensor die along a longitudinal axis. The first and second magnetic sensor dies are angled relative to one another about the longitudinal axis by a fixed non-parallel angle. The integrated device package has a width along a transverse axis that is perpendicular to the longitudinal axis. The width can be in a range of 50 microns to 600 microns.

In some embodiments, the package can also include an elongate bracket extending along the longitudinal axis. The elongate bracket can include a first support surface and a second support surface disposed at the fixed non-parallel angle about the longitudinal axis relative to the first support surface.

In some embodiments, the elongate bracket can include a first bracket component having the first support surface and a second bracket component having the second support surface.

In some embodiments, the package substrate can include one or a plurality of package substrates.

In some embodiments, the package can also include a molding material that fixes the fixed non-parallel angle.

In some aspects, a medical device is disclosed. The medical device includes an elongate body that has a proximal portion and a distal portion spaced from the proximal portion along a longitudinal axis. The medical device also includes an integrated device package coupled with the elongate body. The integrated device package includes a first integrated device die and a second integrated device die spaced from the first integrated device die along the longitudinal axis. The integrated device package has a width along a transverse axis that is perpendicular to the longitudinal axis. The width being in a range of 50 microns to 600 microns. The first and second integrated device dies are angled relative to one another about the longitudinal axis by a fixed non-parallel angle.

In some embodiments, the integrated device package has a length along the longitudinal axis in a range of 1 mm to 8 mm.

In some embodiments, the elongate body can include a catheter, and the integrated device package can be placed in a lumen of the catheter.

In some embodiments, the elongate body can include a guidewire, and the integrated device package can be coupled with the guidewire.

In some embodiments, the medical device can also include a cable extending proximally from the integrated device package along the elongate body, and the cable can be electrically connected to leads of the integrated device package.

In some embodiments, the medical device can also include a controller in electrical communication with the integrated device package. The integrated device package can be configured to transmit a signal to the controller indicative of a position of the integrated device package.

In some embodiments, the controller can include processing electronics configured to analyze the signal to determine the position of the integrated device package.

In some embodiments, the controller can be configured to provide power and ground to the electronic device package by way of one or more cables.

In some embodiments, the first and second integrated device dies can include anisotropic magnetoresistance (AMR) sensor dies.

In some embodiments, the medical device can also include a magnetic generator that can be configured to generate a magnetic field to be sensed by the first and second integrated device dies.

In some embodiments, the magnetic generator can include a plurality of magnetic generators spaced from one another. Each magnetic generator of the plurality of magnetic generators can be configured to generate the respective magnetic field at different frequencies.

In some embodiments, the first and second integrated device dies can be configured to transduce the magnetic field generated by the magnetic generator into respective position signals representative of the respective positions of the first and second integrated device dies. The controller can include processing electronics that can be configured to determine the position of the integrated device package based on a comparison of the respective position signals.

In some embodiments, the medical device can also include a molding material that fixes the fixed non-parallel angle.

In another aspect, another integrated device package is disclosed. The integrated device package includes an elongate bracket extending along a longitudinal axis, a package substrate that has a first portion and a second portion, a first integrated device die mounted to the first portion of the package substrate, and a second integrated device die mounted to the second portion of the package substrate. The elongate bracket includes a first bracket component having a first support surface and a second bracket component having a second support surface. The second support surface is placed at a fixed non-parallel angle about the longitudinal axis relative to the first support surface.

BRIEF DESCRIPTION OF THE DRAWINGS

Embodiments will now be described with reference to the following drawings, which are provided by way of example, and not limitation.

FIG. 3 is a schematic front perspective view of an integrated device package having a bracket assembly coupled with the elongate body and disposed within a lumen in accordance with an embodiment.

FIG. 4 is a schematic rear perspective view of the integrated device package of FIG. 3 disposed within the lumen.

FIG. 5 is a schematic front perspective view of the integrated device package of FIG. 3 outside of the lumen.

FIG. 6 is a schematic end view of the integrated device package disposed within the lumen, as viewed along the longitudinal axis of the package.

FIG. 12 is a schematic front perspective view of the integrated device package including a third integrated device die and at least partially surrounded by a molding material in accordance with another embodiment.

FIG. 13 is a schematic end view of the integrated device package, as viewed along the longitudinal axis of the package, disposed within the molding material.

DETAILED DESCRIPTION

Figure 1:
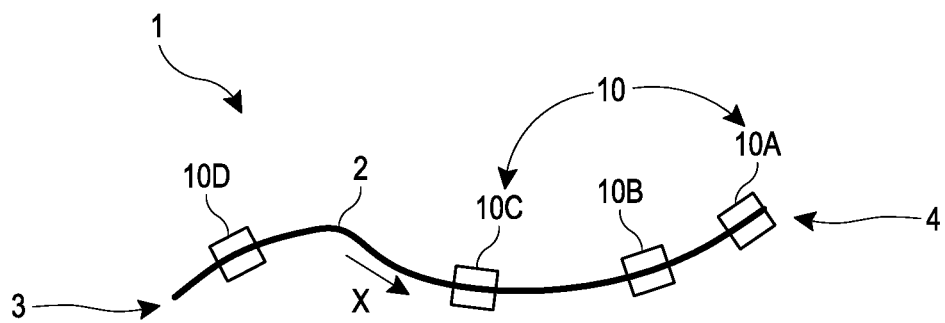
FIG. 1 is a schematic system diagram of a device comprising an elongate body and compact integrated device packages coupled to the elongate body.

Various embodiments disclosed herein relate to integrated device packages that have a compact or low profile and that may be used to sense the location of small devices. For example, various packages disclosed herein can be configured for use in devices that are inserted into a body lumen or body cavity of a human patient. In some embodiments, the integrated device packages are configured to be coupled to a guidewire that is for insertion into a body lumen or body cavity of a human patient. The embodiments disclosed herein may be particularly beneficial for use with systems that are used at a location remote from the clinician and/or access site, e.g., when the treatment or diagnosis location is not easily visible from outside the body. For example, the packages disclosed herein can be used in any suitable type of medical treatment or diagnostic procedure, including, e.g., cardiac catheter-based treatments, pill-based diagnostic and treatment techniques, endoscopy treatments, urinary catheters and endoscopes, ultrasonic imaging catheters, ear-nose-and-throat based catheters, gastroenterology treatments, colonoscopy treatments, etc. With respect to cardiac treatments, the packages disclosed herein can be used in cardiac diagnostic catheters, die delivery catheters, catheter-based pumps, optical coherence tomography (OCT) catheters, valve delivery catheters, intracardiac echocardiography (ICE) catheters, transesophageal echocardiography (TEE) catheter, diagnostic catheters, PICC lines or any other suitable device. In some embodiments, the packages disclosed herein can be coupled with the guidewire, in addition to, or as an alternative to, coupling the package to the catheter.

In various medical procedures having treatment locations remote from the clinician and/or access site, it can be important to monitor the position and/or the orientation of a working end of the medical device, e.g., the portion of the medical device that interacts with the treatment or diagnosis region. However, in many situations, it can be challenging to package sensors in a sufficiently compact profile to enable insertion into the anatomy. Similarly, in other applications compact location sensors are desirably associated with small tools or devices, particularly to aid precise positioning of such tools or devices in three dimensions.

To package the sensors provided on the working end such that the sensors can be inserted into the anatomy, in some embodiments, the working end can be included on an elongate bracket assembly. The elongate bracket assembly can be comprised of one or more brackets. The brackets may be separated along the longitudinal axis. Accordingly, various embodiments herein provide an elongate bracket assembly extending along a longitudinal axis of the tool or device. The elongate bracket assembly can include a first support surface and a second support surface disposed at a fixed non-parallel angle about the longitudinal axis relative to the first support surface. The fixed non-parallel angle can be about 90° in some arrangements, e.g., in a range from 89° to 91°, or in a range from 89.5° to 90.5°. A package substrate can comprise a first portion and a second portion, the first portion mechanically connected to the first support surface and the second portion mechanically connected to the second support surface. A first integrated device die can be mounted to the first portion of the package substrate. A second integrated device die can be mounted to the second portion of the package substrate. Thus, the first and second device dies can be disposed relative to one another at the fixed non-parallel angle.

In some arrangements, each of the first and second device dies comprises a magnetic sensor, such as an anisotropic magnetoresistance (AMR) sensor, a tunneling magnetoresistance (TMR) sensor, or a giant magnetoresistance (GMR) sensor. In various embodiments, the first die can measure the position of the package along two coordinates, and the second device die can measure the position of the package along a third coordinate. Angling the device dies relative to one another by way of deforming the package substrate can beneficially enable three-dimensional position detection of the package within the anatomy. For example, the two dies can be angled approximately perpendicular to one another to enable position sensing along three orthogonal axes. The sensor packages disclosed herein can be used in various applications, including medical devices or other technologies in which sensors are provided in small spaces. For example, in medical device implementations, the sensors can be used to sense various characteristics of the human body. Although the embodiments disclosed herein relate to position sensing, it should be appreciated that other types of sensors may be used, such as sensors that detect velocity, acceleration (e.g., accelerometers), orientation (e.g., gyroscopes), temperature, pressure, pH, etc.

FIG. 1 is a schematic system diagram of a device 1, such as a medical device, comprising an elongate body 2 having a proximal portion 3 and a distal portion 4 spaced from the proximal portion 3 along a longitudinal axis x. The longitudinal axis x may be defined in local coordinates of the elongate body 2, and may not necessarily correspond to fixed Cartesian coordinates. The elongate body 2 can comprise a medical device, such as a catheter or a guidewire. The device 1 can comprise one or a plurality of compact integrated device packages 10, such as packages 10A, 10B, 10C, 10D, coupled with the elongate body 2. The packages 10 can be disposed in a lumen of the elongate body 2, or can be attached to an outside surface of the elongate body 2. In some embodiments, only a single device package 10 may be coupled with the elongate body 2. In the example of a surgically or percutaneously implemented medical device, the device package 10 can be configured to provide the clinician with an indication of the position of the package 10 (and hence the portion of the elongate body 2 to which the package 10 is coupled) within the patient's anatomy. The indicated position can be provided relative to a three-dimensional coordinate system in some embodiments, so that the clinician can beneficially determine the precise location of the working end and/or a path of the elongate body 2 within the body.

In other embodiments, a plurality of device packages 10 may be disposed along a length of the elongate body 2. Utilizing a plurality of packages 10 (such as packages 10A-10D) may advantageously provide the clinician with position information of different portions of the elongate body 2. Information about the position of multiple portions of the elongate body 2 can assist the clinician in positioning the working end of the elongate body 2 relative to the anatomy. For example, in medical device applications, multiple packages 10 can be used to guide different branches of the elongate body 10 into lateral vessels (such as Y-shaped branches), and/or to position the elongate body 10 (or portions thereof) across a cardiac valve.

Figure 2:
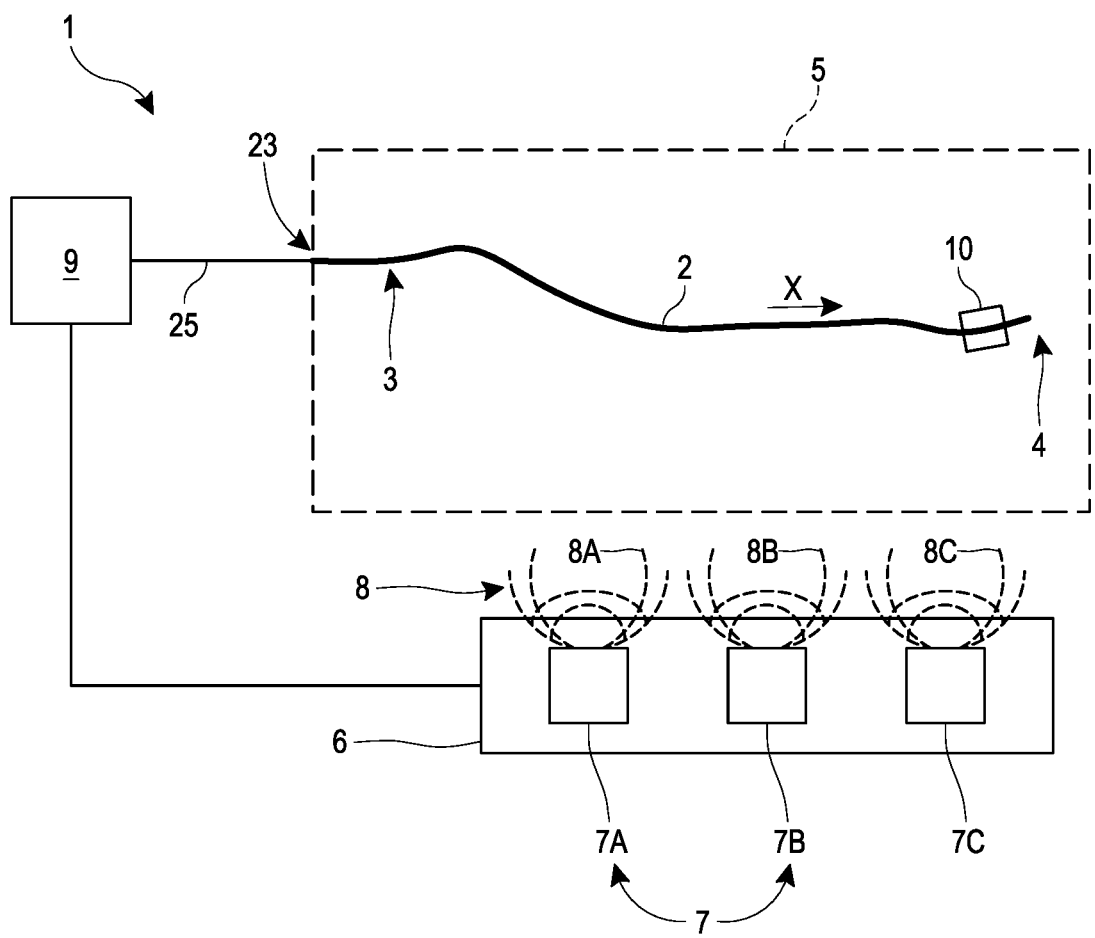
FIG. 2 is a schematic system diagram of the device during use in a procedure.

FIG. 2 is a schematic system diagram of the device 1 during use in a procedure, according to various embodiments. The device 1 can include the elongate body 2 shown in FIG. 1, with only a single integrated device package 10 coupled with the elongate body 2. It should be appreciated that multiple packages 10 can also be used in connection with FIG. 2. As shown in FIG. 2, the elongate body 2 can be disposed within an object 5 during a procedure, such as within a body of a human patient during a treatment or diagnostic procedure. During the procedure, the proximal portion 3 can be disposed at or near an access site 23 (such as the femoral artery for cardiac catheterization procedures). One or more conduits 25 can connect the proximal portion 3 of the elongate body 2 with a console 9. The one or more conduits 25 may comprise one or more fluid conduits configured to deliver fluid to and/or remove fluid from the elongate body 2. The one or more conduits 25 may also include one or more electrical cables to provide electrical communication between the console 9 and various electrical and electronic components of the elongate body 2 (including, e.g., the package 10).

For example, the console 9 can comprise a controller that can provide power and/or ground to the device package 10 by way of the one or more conduits 25 (e.g., electrical cables). The controller can comprise processing electronics configured to control the operation of the device 1. For example, the processing electronics can be programmed by way of software to implement instructions that operate the device 1. The console 9 may also include various fluid reservoirs, pumps, sensors, and other devices used in connection with the operation of the device 1. The console 9 can transmit signals to and receive signals from the package 10 at the working end of the device 1. In various embodiments, the console 9 can comprise a user interface (such as a display or touch-screen display, a keypad, etc.) that informs the clinician about the status of the procedure and/or the location of the working end of the device 1. The clinician can input instructions to the console 9 by way of the user interface to select various settings and/or operational modes of the device 1 during and/or before use. In some embodiments, the console 9 can be connected to an external processing device (e.g., a computer) that can, for example, act as the user interface and/or analyze operation data. In some embodiments, the console 9 can receive the signals from the package 10, and can provide feedback to the package 10 with further instructions based on the received signals.

In some embodiments, as explained herein, the package 10 can comprise a position sensor package configured to determine an approximate position of the package 10, and therefore the portion of the elongate body 2 to which the package is connected. In some embodiments, for example, the package 10 can comprise a magnetic sensor package, and particularly a magnetoresistance sensor package, e.g., an anisotropic magnetoresistance (AMR) sensor package, a tunneling magnetoresistance (TMR) package, or a giant magnetoresistance (GMR) package. For example, AMR packages, such as the packages 10 disclosed herein, can comprise a plurality of AMR sensor dies having an anisotropic material in which electrical resistance depends on an angle between the direction of electrical current and the direction of the magnetic fields sensed by the anisotropic material. In some arrangements, for example, the resistance may be maximized when the direction of current is parallel to the magnetic field, and the resistance may be reduced at other angles.

As shown in FIG. 2, a magnetic generator 7 may be provided with the device 1 so as to generate a magnetic field 8 to be transduced by the package 10. The magnetic generator 7 may comprise one or a plurality of magnetic generators, each of which may comprise one or a plurality of coiled wires. In the illustrated embodiment, for example, the magnetic generator 7 comprises a plurality of magnetic generators 7A, 7B, 7C spaced from one another by predetermined spacings. Each magnetic generator 7A-7C of the plurality of magnetic generators can be configured to generate a respective magnetic field 8A-8C at different frequencies. In some arrangements, the console 9 can control the operation of the magnetic generator 7, while in other embodiments, the magnetic generator 7 may be controlled separately from the console 9 to which the elongate body 2 is connected. The generated magnetic fields 8A-8C may be sufficiently strong so as to penetrate the object 5 and to be sensed by the package 10. For example, in some embodiments, the object 5 (e.g., human patient) may lie on a table, with the magnetic generators 7A-7C disposed under the table and object 5.

In various embodiments, the package 10 can be configured to detect the generated magnetic fields 8A-8C. The integrated device package 10 can be configured to transmit a signal to the controller of the console 9 that is indicative of a position of the integrated device package 10. The package 10 can comprise one or a plurality of integrated device dies that can detect the components of the magnetic fields 8A-8C in three dimensions. The signal can be transmitted to the controller by way of the conduit(s) 25. The controller can include processing electronics configured to analyze the signal to determine the position of the integrated device package 10. For example, the controller can be configured to compare the signal transmitted by the package 10 with the data about the fields 8A-8C generated by the magnetic generators 7A-7C, and/or to compare the signals transmitted from each die of the package 10 with one another. In some embodiments, the magnetic fields 8A-8C may comprise different frequencies that are detectable by the processing electronics. The controller can therefore associate each of the fields 8A-8C detected by the package 10 with an associated magnetic generator 7A-7C, based at least in part on the associated frequency of the fields 8A-8C. The known positions of the magnetic generators 7A-7C in a global set of Cartesian coordinates (e.g., X, Y, Z) set by the console 9 can be used to triangulate the position, rotation, and/or orientation of the package 10 in and about three dimensions. The processing electronics of the controller can therefore be configured to determine the position of the integrated device package 10 based on a comparison of the respective position signals of each sensor die in the package 10. In some arrangements, the differential output signals from the dies may comprise a pair of twisted wires or a pair of wires spaced closely to one another. Such an arrangement may beneficially reduce any inductance from the magnetic generator 7 in the differential output signal.

FIG. 3 is a schematic front perspective view of the integrated device package 10 coupled with the elongate body 2, according to various embodiments. FIG. 4 is a schematic rear perspective view of the package 10 of FIG. 3. In the embodiment of FIGS. 3 and 4, the package 10 is shown inside a lumen 11 of the elongate body 2 (which may have a single lumen or multiple different lumens therein). In some embodiments, the package 10 is disposed inside of a lumen of a catheter. In other embodiments, however, the package 10 can be disposed on an outer surface of the elongate body 2, or otherwise coupled with the elongate body 2, or could be employed independently of any lumens. The elongate body 2 as shown in some Figures has a cylindrical shape but the elongate body 2 may have any suitable shape for receiving or coupling to the package 10.

Figure 7:
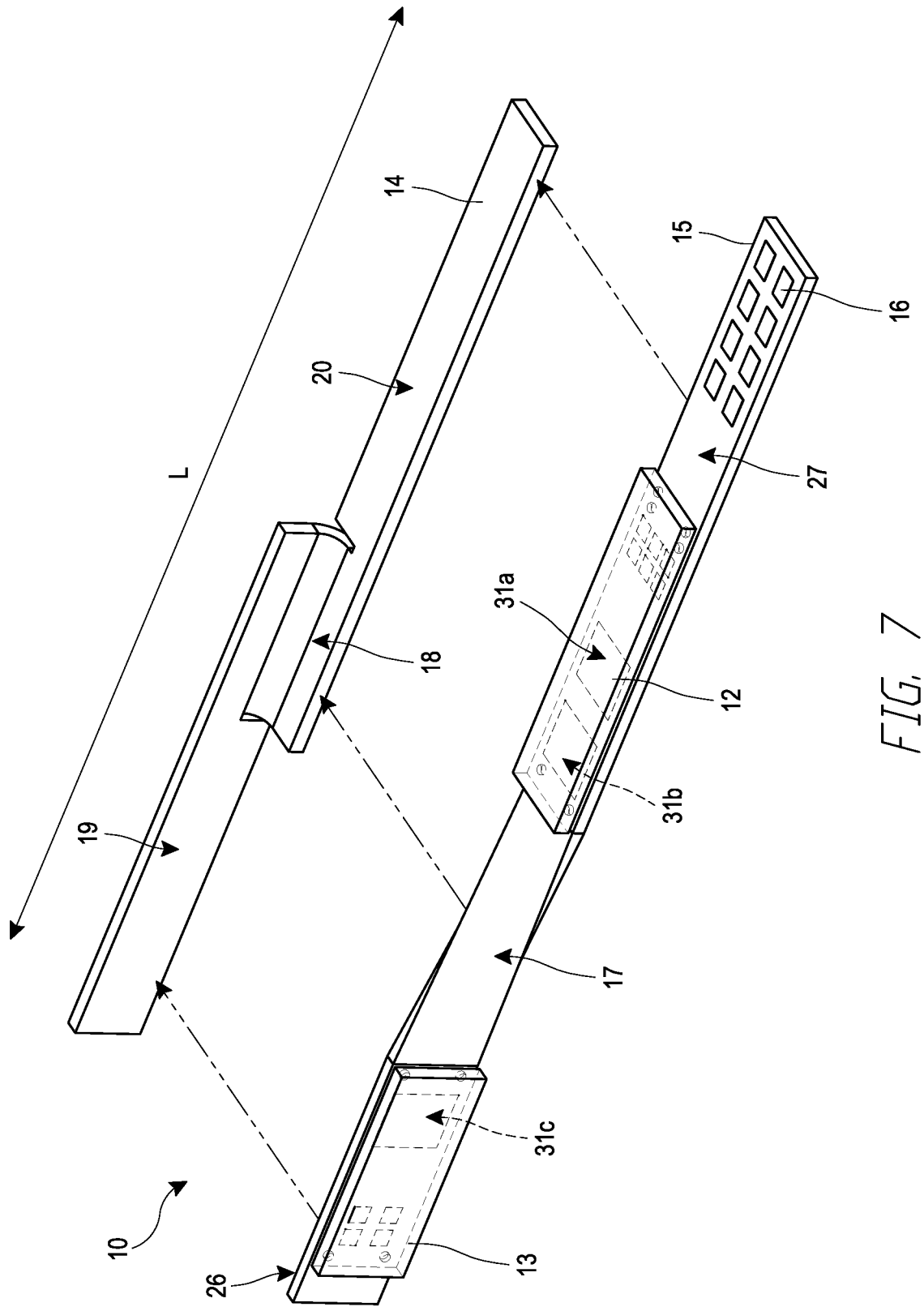
FIG. 7 is a schematic perspective exploded view of the integrated device package of FIG. 5.

FIG. 5 is a schematic front perspective view of the integrated device package 10. FIG. 6 is a schematic end view of the integrated device package 10, as viewed along the longitudinal axis of the package 10, with the package 10 shown disposed within the lumen 11 of the elongate body 2. FIG. 7 is a schematic perspective, exploded view of the integrated device package 10. As shown in FIGS. 3-7, the package 10 can comprise an elongate bracket assembly 14 extending along a longitudinal axis x, the elongate bracket assembly 14 comprising a first support surface 19 and a second support surface 20 disposed at a fixed non-parallel angle about the longitudinal axis x relative to the first support surface 19. The longitudinal axis x may be defined in local coordinates of the integrated device package 10, and may not necessarily correspond to fixed Cartesian coordinates. For example, the first and second support surfaces 19, 20 can be disposed generally perpendicular to one another about the longitudinal axis x. A package substrate 15 can include a first portion 26 and a second portion 27, the first portion 26 mechanically connected to the first support surface 19 and the second portion 27 mechanically connected to the second support surface 20. For example, the first and second portions 26, 27 can be adhered to the first and second support surfaces 19, 20 of the bracket assembly 14 by way of an adhesive.

A first integrated device die 13 can be mounted to the first portion 26 of the package substrate 15. A second integrated device die 12 can be mounted to the second portion 27 of the package substrate 15. For example, the first and second device dies 13, 12 can be attached to the substrate 15 using a suitable die attach material. As shown in FIG. 3-7, the first and second device dies 13, 12 can be spaced from one another along the longitudinal axis x of the package 10. The first and second device dies 13, 12 can comprise any suitable type of device die, such as a motion or position sensor die, a processor die, a microelectromechanical systems (MEMS) die, etc. In the illustrated embodiment, the first and second dies 13, 12 comprise magnetic sensor dies, e.g., magnetoresistance sensors such as AMR, GMR, or TMR sensor dies, that can serve as position and/or rotation sensors in combination with known external magnetic field source(s). For example, the first integrated device die 13 can be configured to sense a position and/or orientation of the package 10 along and about first and second orthogonal axes (e.g., X and Y axes), and the second integrated device die 12 can be configured to sense the position and/or orientation of the package 10 along and about a third axis (e.g., Z axis) orthogonal to the first and second axes, or vice versa. For example, as shown in FIG. 7, the first die 13 can have first and second sensing regions 31a, 31b that are configured to sense the position and orientation of the package 10 along and about X and Y axes, respectively. The second die 12 can have a third sensing region 31c that is configured to sense the position and orientation of the package 10 along and about the Z axis. The sensing regions 31a-31c may be sensitive to magnetic fields, as described above, and can estimate the position and/or orientation of the dies 13, 12 based on the detected magnetic field. In some embodiments, the sensing regions 31a-31c may be separated within the package 10 by various non-magnetic materials. For example, the portions of the dies 13, 12, and/or the portions of the substrate 15 (such as the twisted section 17), that intervene between the regions 31a-31c may be non-magnetic. Similarly, the bracket assembly 14 may be non-magnetic. While FIGS. 3, 5, and 7 show the die 13 having one sensing region 31a, and the die 12 having two sensing regions 31b, 31c, the dies 13, 12 can have any suitable number of regions. Further, the die 13 as shown in FIGS. 3, 5, and 7 includes the sensing region 31c at a distal portion of the die 13, but the region 31c may instead be disposed nearer a proximal portion of the die 13 (e.g., the die 13 could be rotated by 180° about an axis perpendicular to the major surface of the die 13). Such an alternative arrangement may position contact pads of the die 13 nearer the proximal portion of the die 13 may reduce substrate costs and noise coupling into the sensing region 31c.

In embodiments that utilize AMR sensor dies for the first and second device dies 13, 12, it can be important to dispose the dies 13, 12 at a fixed angle relative to one another, so that the active surfaces of the dies 13, 12 are at a known angle. By angling the dies 13, 12 relative to one another about the longitudinal axis x of the package 10, the three-dimensional position of the package 10 can be calculated. For example, in the illustrated embodiment, the dies 13, 12 can be angled relative to one another about the longitudinal axis x by a fixed non-parallel angle of about 90°, e.g., in a range of 89° to 91°, or in a range of 89.5° to 90.5°. However, it should be understood that in various other embodiments the fixed non-parallel angle can be any angle so long as the AMR sensor dies detect enough difference in magnetic field to accurately calculate the three-dimensional position of the package 10.

To enable the precise relative angular orientation of the dies 13, 12, in some embodiments, the bracket assembly 14 can provide a stiff support structure to support the integrated device dies 13, 12. For example, the bracket assembly 14 can include a transverse portion 18 disposed between and connecting the first and second support surfaces 19, 20. The transverse portion 18 can act as a transition to precisely orient the first and second support surfaces 19, 20 by the fixed non-parallel angle. However, in some embodiments, the transverse portion 18 may be eliminated. In such embodiments that do not comprise the transverse portion 18, the bracket assembly 14 can comprise multiple bracket components that are spaced and/or separated, for example, brackets 14a, 14b shown in FIG. 8, as explained below. The bracket assembly 14 can comprise a non-magnetic material in some embodiments, such as copper or aluminum. The bracket assembly 14 can be shaped from a single piece of material in some embodiments. In some other embodiments, multiple pieces can be connected to define the bracket assembly 14. The angled surfaces 19, 20 can be precisely positioned, which can advantageously lower the resolution and increase the dynamic range of the sensor dies.

In some embodiments, the package substrate 15 can comprise a single package substrate sufficiently flexible to comprise one or more bends. For example, in the illustrated embodiment, the package substrate 15 can comprise one or more bends that enable the substrate 15 to conform to the angled surfaces 19, 20 of the bracket assembly. As shown in FIGS. 3, 5, and 7, for example, the substrate 15 can comprise a twisted section 17. The twisted section 17 can be disposed between the first portion 26 and the second portion 27 of the substrate 15 so as to position the first and second portions 26, 27 at the fixed non-parallel angle relative to one another. It should be understood that, for some embodiments, the twisted section 17 may not be fixed in all directions as long as the relative angle of the portions 26, 27 is fixed. For example, in some embodiments the first and second portions 26, 27 may be allowed to bend relative to one another about an x-z line or about an x-y line. The package substrate 15 can comprise a laminate substrate in some embodiments, with conductors embedded in an insulator. In some embodiments, the package substrate 15 can comprise a plurality of substrates. For example, in such embodiments, the first and second portions 26, 27 can be defined by separate substrates that may or may not be connected to one another. The substrate 15 can be sufficiently flexible such that the bend(s) (e.g., the twisted section 17) can be formed by a user or a machine applying a twisting force to the substrate 15 about the longitudinal axis x without breaking and/or shorting internal conductors. When assembled, the portions of the substrate 15 that are not attached to the bracket assembly 14 (including, e.g., the twisted portion 17) may remain flexible so as to be compressed and/or bent to accommodate different package geometries. In various embodiments, the package substrate 15 can comprise a flexible insulator (e.g., polyimide) with embedded metal traces that provide electrical connectivity through the substrate 15.

The package substrate 15 can comprise a plurality of conductive leads 16 configured to provide electrical communication with a cable or other interconnect that connects with the console 9. In the illustrated embodiment, for example, there may be eight leads 16 configured to provide connections for ground, power, and six signal lines. The six signal lines may comprise two terminals for each position signal to be transduced. For example, in the three-dimensional position sensor package 10 shown herein, two leads 16 may be provided for each Cartesian coordinate (X, Y, Z). The two device dies 13, 12 may be electrically connected to one another through the substrate 15 in some embodiments. In other embodiments, the dies 13, 12 are not electrically connected to one another. In the illustrated embodiment, the conductive leads 16 may be disposed proximal the dies 13, 12.

The integrated device dies 13, 12 may be mechanically and electrically connected to the substrate 15 in any suitable manner. For example, as shown in FIG. 6, the dies 13, 12 may be flip chip mounted to the substrate 15 by way of a plurality of solder balls 21. In some embodiments, the dies 13, 12 can be connected to the substrate 15 by way of anisotropic conductive film, non-conductive paste, or a thermocompression bond. In some embodiments, the dies 13, 12 can be wire bonded to the substrate 15 using conductive bonding wires. The substrate 15 may be densely patterned in various arrangements, and can be bendable so as to form the twisted section 17. In some embodiments, the package 10 may be disposed in a package housing or package body (not shown). For example, the package 10 illustrated in FIGS. 3-7 may be entirely or partially encapsulated with a molding material 32 in some embodiments so as to protect the components from fluids and other materials during use and/or to fix the fixed non-parallel angle. The molding material 32 can be any suitable material, e.g., thermosetting or ultraviolet (UV) cured epoxy, injection molded compound, transfer molded compound, glob top, laminated layers, gravity poured epoxies, melted sheets, encapsulant, plastic, etc.

In some procedures, the elongate body 2 may be guided through various curves and bends, such as through parts of the anatomy for medical diagnostic or treatment procedures. It can be important to ensure that the elongate body 2 is sufficiently flexible so as to traverse such non-linear paths. Accordingly, it can be important to provide a package 10 that minimizes a length L of the bracket assembly 14, since the bracket assembly 14 may drive the overall stiffness of the package 10 (see FIG. 7). In some embodiments, length L of the bracket assembly 14 along the longitudinal axis x can be no more than 8 mm, e.g., in a range of 1 mm to 8 mm, in a range of 1 mm to 6 mm, in a range of 2 mm to 6 mm, or in a range of 3 mm to 5 mm. Dimensioning the bracket assembly 14 and the package 10 to have a short stiff length can enable the elongate body 2 to traverse curved pathways in the body.

The elongate body 2 has a diameter d for receiving or coupling the package 10 within the body 2, as viewed along the longitudinal axis x of the package 10 (see FIG. 6). The diameter d can be in a range of 0.6 millimeters to 2.5 millimeters, in a range of 1 millimeter to 2.5 millimeters, or in a range of 1 millimeter to 2 millimeters.

Moreover, it can be important to provide the package 10 with a width that is small enough to be inserted into small spaces for the application of interest, such as a body lumen or cavity of the patient. For example, the molding material 32 that surrounds the package 10 can have a width W along a transverse axis that is perpendicular to the longitudinal axis x. The width W defines the largest transverse dimension of the package. In case of the embodiment illustrated in FIG. 6, the width W corresponds to the diameter of the molding material 32 because the molding material 32 has a cylindrical shape. The width W can be in a range of 300 microns to 800 microns, in a range of 400 microns to 800 microns, or in a range of 400 microns to 600 microns (see FIG. 6). The width W can represent the largest extent of the package 10 along the direction transverse to the longitudinal axis x. The diameter d of the elongate body 2 may determine the maximum width W of the molding material 32 for the package 10.

In some embodiments, additional integrated device dies and electrical components may be provided in the package 10. For example, in some embodiments, a third integrated device die (such as a processor die, an amplifier, a filter, an analog-to-digital converter (ADC), etc.) can be mounted to the substrate 15 along the first or second portions 26, 27 (see, e.g., the die 28 of FIG. 12). The third integrated device die can process signals transmitted from the first and second dies 13, 12. For example, in some embodiments, the third die 28 can provide various pre-processing capabilities (e.g., analog to digital conversion and/or signal amplification) in the package 10, which can increase the accuracy of the measurements. Positioning the third die 28 (see the die 28 of FIG. 12) within the package 10 near the dies 13, 12 can beneficially reduce signal losses caused by directing the signals to the console 9 without any pre-processing. The three device dies 13, 12, 28 may be electrically connected to one another through traces embedded in the substrate 15.

In some embodiments, the substrate 15 can extend beyond the bracket assembly 14 along the longitudinal axis x. For example, as shown in FIGS. 3 and 5, the substrate 15 may extend beyond the bracket assembly 14 so as to provide electrical communication between electrical cables and the leads 16. In some embodiments, the package substrate 15 can extend within the elongate body 2 for a substantial distance. For example, the package substrate 15 can extend proximally from the package 10 to the proximal portion 3 of the device 1. In other embodiments, the package substrate 15 can extend at least halfway from the package 10 to the proximal portion 3. In still other embodiments, the package substrate 15 can extend at least a third or at least a quarter of the distance from the package 10 to the proximal portion 3.

In such arrangements, the extended length of the package substrate 15 can enable the integration of additional integrated device dies and electrical components into the device 1. For example, in some embodiments, it may be preferable to position additional device dies (such as the third die referenced above) at a distance from the package 10 so as to reduce the amount of heat generated by the package 10. In some cases, if too many electrical components are provided in a small space, the increased temperature due to power dissipation can be undesirable for the application of interest, such as use in a patient's body for medical diagnostic or treatment applications. Spreading the additional device dies (such as processing dies) along the length of the device 1 and connected with an extended length substrate 15 can beneficially disperse the generated heat so that the temperature in a particular location does not appreciably increase. Furthermore, even though the additional dies may not be disposed within the package 10, the additional dies may still be nearer the package 10 than they otherwise would be if housed in the console 9. Positioning the additional dies between the proximal portion 3 of the device 1 and the package 10 can therefore improve the signal quality of the sensed position data while maintaining the desired temperature.

Figure 8:
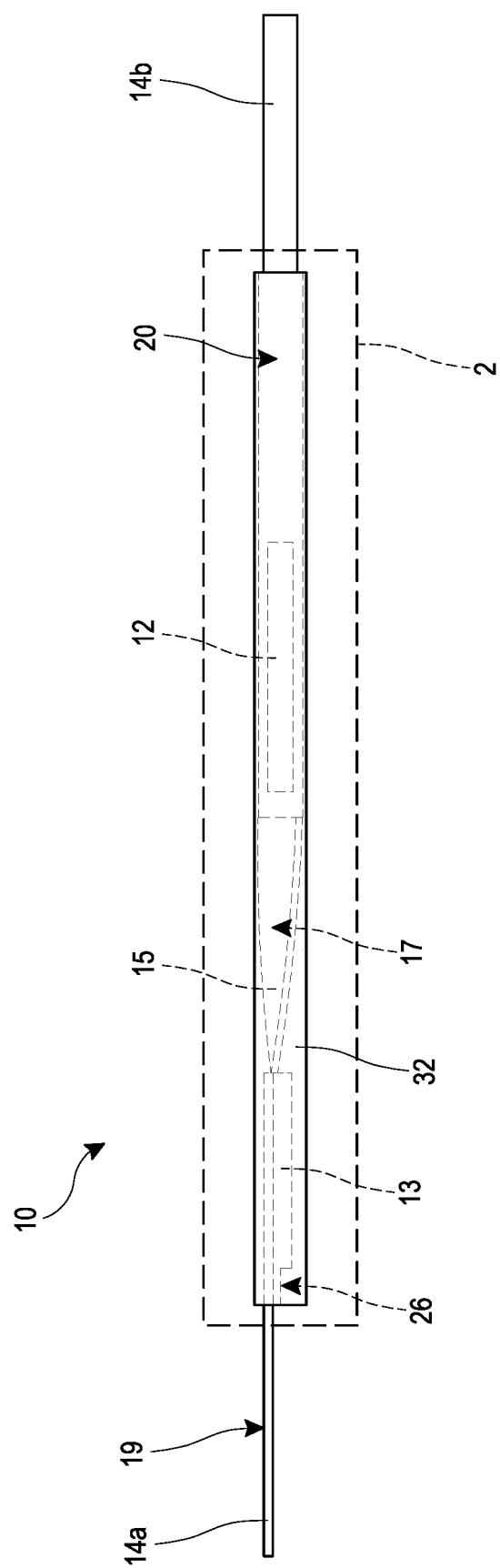
FIG. 8 is schematic front view of the integrated device package having a bracket assembly, in accordance with another embodiment.
Figure 9:
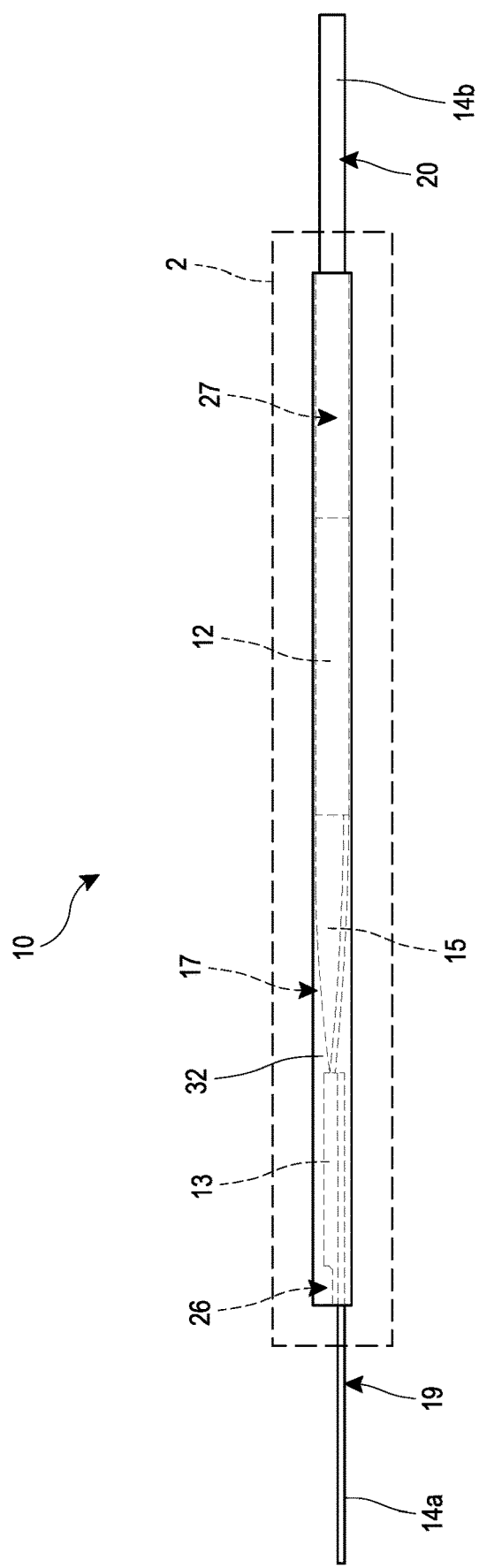
FIG. 9 is schematic backside view of the integrated device package of FIG. 8.

FIGS. 8-9 illustrate another embodiment of a device 1 having a package 10 with a plurality of integrated device dies 13, 12 angled relative to one another by a fixed angle. Unless otherwise noted, components of FIGS. 8-9 are the same as or generally similar to like-numbered components shown in FIGS. 1-7. FIG. 8 is a schematic front view of an integrated device package 10 having a substrate 15 and integrated device dies 13, 12, mounted thereto. As with the embodiment of FIGS. 1-7, the substrate 15 can be mounted to a bracket assembly 14. However, unlike the embodiment of FIGS. 1-7, the bracket assembly 14 may comprise multiple brackets 14a, 14b that are separated and spaced from one another, e.g., the bracket assembly 14 may omit the transverse portion 18 shown, e.g., in FIG. 4. FIG. 9 is schematic rear view of the integrated device package 10 of FIG. 8.

In FIGS. 8 and 9, the integrated device package 10 has separated brackets 14a, 14b that define the bracket assembly 14. The brackets 14a, 14b depicted in FIGS. 8 and 9 are separate from and spaced from each other along the longitudinal axis x. The bracket 14a has a first support surface 19 and the bracket 14b has a second support surface 20. The substrate 15 can include a first portion 26 and a second portion 27, the first portion 26 mechanically connected to the first support surface 19 and the second portion 27 mechanically connected to the second support surface 20. For example, the first and second portions 26, 27 can be adhered or bonded to the first and second support surfaces 19, 20, respectively, by way of an adhesive. The first integrated device die 13 can be mounted to the first portion 26 of the package substrate 15. The second integrated device die 12 can be mounted to the second portion 27 of the package substrate 15. In some embodiments, the bracket assembly 14 can have more than two brackets 14a, 14b. While shown for purposes of illustration with ends of the two brackets 14a, 14b protruding out of the elongate body 2, it will be understood that in use the entire package 10 can be within the elongate element 2.

As shown in FIGS. 8 and 9, similar to the embodiment of FIGS. 1-7, the substrate 15 can comprise a twisted section 17. The twisted section 17 can be disposed between the first portion 26 and the second portion 27 of the substrate 15 and be twisted about the longitudinal axis so as to position the first and second portions 26, 27 at a fixed non-parallel angle relative to one another. The twisted section 17 may also be disposed between the brackets 14a, 14b to connect the brackets 14a, 14b. However, unlike the embodiment of FIGS. 1-7, the twisted section 17 may not be connected to a corresponding twisted or transverse portion of the bracket assembly 14. Unlike the embodiment of FIGS. 1-7, in which the twisted section 17 can couple with the transverse portion 18, the twisted section 17 of FIGS. 8-9 may be unconnected to the bracket assembly 14 since the bracket assembly 14 may not include the transverse portion 18.

The bracket assembly 14 having the brackets 14a, 14b can provide a stiff support structure to support the integrated device dies 13, 12. In some embodiments, the fixed angle between the dies 13, 12 can be provided by applying a molding material 32 over the dies 13, 12. The molding material 32 can be disposed entirely or partially around the package 10 to define the fixed non-parallel angle and/or protect the components from fluids and other materials during use. In some embodiments, the mold 32 may entirely envelope the twisted section 17, and only partially envelope the brackets 14a, 14b. As previously discussed, the fixed non-parallel angle can be about 90° in some arrangements, e.g., in a range from 89° to 91°, or in a range from 89.5° to 90.5°. However, as also explained above, in other embodiments, the fixed non-parallel angle can comprise other numerical values.

Embodiments of the package 10 with the bracket assembly 14 that do not include the transverse portion 18 of FIGS. 1-7 can be beneficial because the overall size of the package 10 of FIGS. 8-9 can be smaller than the overall size of the package 10 of FIGS. 1-7 that includes the transverse portion 18. Referring back to FIGS. 6 and 7, the first and second support surfaces 19, 20 of the bracket assembly 14 form an L-shape. In such embodiments deforming (e.g., twisting) the substrate 15 and/or the dies 13, 12 depends on the shape and dimensions of the bracket assembly 14. However, by omitting the transverse portion 18, the package 10 may be deformed more freely at the twisted section 17 of the substrate 15 and would not be limited to the L-shape. Thus, the width W of the molding material 32 for the package 10 after deformation can be generally similar to the width W before deformation, which can beneficially enable the package 10 to fit within the elongate body 2.

Figure 10:
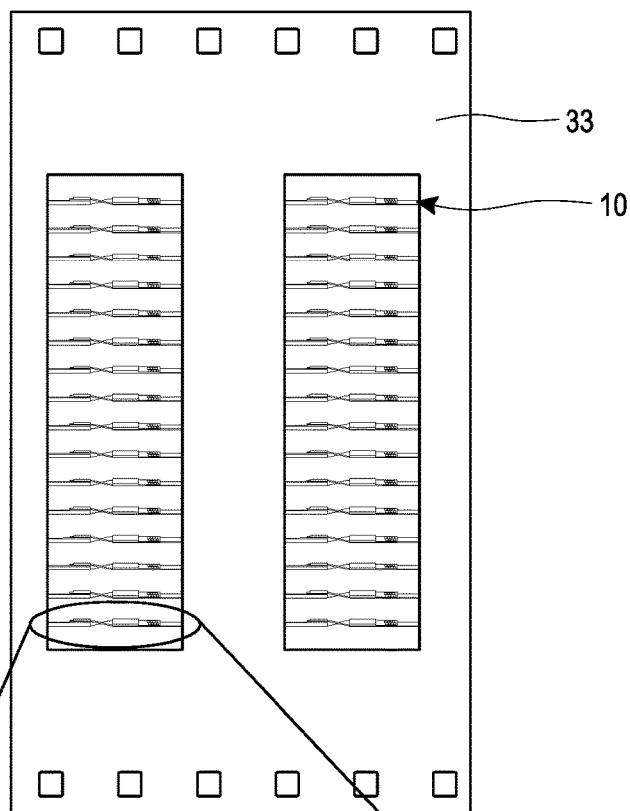
FIG. 10 is a top perspective view of the integrated device packages coupled with a frame during a manufacturing process.
Figure 11:
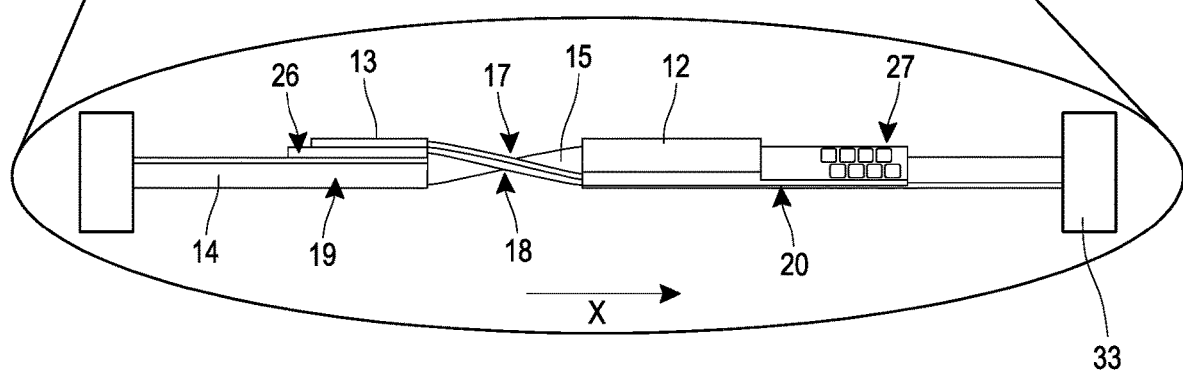
FIG. 11 is an enlarged view of an exemplary integrated device package of FIG. 10 shown with portions of the frame.

FIG. 10 is a top perspective view of the integrated device packages 10 coupled with a frame 33 during a process for manufacturing the package 10, according to the embodiments of FIGS. 1-9. FIG. 11 is an enlarged view of an exemplary integrated device package 10 of FIG. 10 coupled with portions of the frame 33. The frame 33 may comprise a metal frame or any suitable frame to assist in simultaneously manufacturing numerous packages. In some embodiments, one or multiple substrates 15 can be placed on bracket assembly 14, corresponding to portions of the frame 33. In some embodiments, such as the embodiment of FIGS. 1-7, the bracket assembly 14 can include a transverse portion 18 disposed between and connecting the first and second support surfaces 19, 20. However, as explained above, the transverse section 18 may be omitted and have brackets 14a and 14b as shown in FIGS. 8-9. When there is no transverse portion 18, the bracket assembly 14 can, for example, comprise brackets 14a, 14b separated from and/or spaced from each other along the axis x. The integrated device packages 10 can be separated from the frame 33 by punching, sawing, laser cutting or any other suitable methods of dividing the frame 33.

FIGS. 12-15 illustrate another embodiment of a device having an integrated device package 10 with dies 13, 12 that are angled relative to one another by a fixed non-parallel angle. Unlike the embodiments of FIGS. 1-11, in which the substrate 15 is coupled to a bracket assembly 14, in FIGS. 12-15, the package 10 may not include a bracket assembly 14. FIG. 12 is a schematic front perspective view of the integrated device package 10 partially surrounded by the molding material 32, according to various embodiments. FIG. 13 is a schematic end view of the integrated device package 10 with molding material 32 surrounding the package 10, as viewed along the longitudinal axis x of the package 10. A third integrated device die 28 (which may comprise an Application Specific Integrated Circuit, or ASIC) may be mounted to the substrate 15 proximal the dies 13, 12, and may electrically connect to the dies 13, 12 through the substrate 15.

In the embodiment of FIG. 12, the package 10 is shown inside various portions of the molding material 32. As shown, the molding material 32 may be applied separately around the device dies 13, 12, and the third die 28. Thus, a first portion of the molding material 32 may be applied over both dies 13, 12, and a second portion of the molding material may be applied over the third die 28. In the illustrated embodiment, the molding material 32 may not be applied around a section 30 of the substrate 15 which can beneficially improve the flexibility of the package 10. Thus, in the illustrated embodiment, the uncovered section 30 of the substrate 15 can enable the package 10 to traverse curved or non-linear sections of the anatomy. However, in other embodiments, the molding material 32 may be applied around the section 30 such that the molding material 32 is disposed about the entire package 10.

The embodiment shown in FIG. 12, which is generally similar to the embodiments shown and described in FIGS. 3-7, can comprise the substrate 15 with leads 16, and the first and second integrated device dies 13, 12 can be mechanically and electrically connected to the substrate 15. The embodiment in FIG. 12 further includes the third integrated device die 28 (such as a processor die, an amplifier, a filter, an analog-to-digital converter (ADC), etc.) mounted to the substrate 15 along the first or second portions 26, 27. The third integrated device die 28 can process signals transmitted from the first and second dies 13, 12. For example, in some embodiments, the device dies 13, 12 can be magnetoresistance sensors such as AMR, GMR, or TMR sensor dies and the third device die 28 can be an ADC. By angling the dies 13, 12 relative to one another about the longitudinal axis x of the package 10, the three-dimensional position of the package 10 can be calculated. In such embodiments, the dies 13, 12 can transmit the sensed data signal to the third die 28 (e.g. an ADC) for converting the sensed analog signal to a digital signal. The processed signal from the third die 28 can be sent via the plurality of conductive leads 16 and a cable or other interconnects to the console 9. By processing the signals very close to the sensors, degradation of the signals through transmission losses can be avoided.

As explained above, the package 10 in FIGS. 12 and 13 does not include the bracket assembly 14, as shown in embodiments in FIGS. 3-7, or the assembly without the transverse portion 18 (i.e., the brackets 14a, 14b), as shown in embodiments in FIGS. 8 and 9. Rather, in FIGS. 12-13, the dies 13, 12 are mounted to the substrate 15, and a molding material 32 is disposed about portions of the dies 13, 12 and the substrate 15 to fix the dies 13, 12 at the fixed non-parallel angle. Thus, unlike the embodiment shown in FIGS. 1-7, the molding compound 32, rather than a bracket assembly 14 or other structure, effects or defines the fixed non-parallel angle between the dies 13, 12. In addition, the third integrated device die 28 can be spaced from the first integrated device die 12 by the section 30 of the substrate 15 along the longitudinal axis x. The section 30 of the substrate 15 shown in FIG. 12 is substantially flat. However, it should be understood that the section 30 may form any shape. In some embodiments, the section 30 can be fixed by applying the molding material 32. In the illustrated embodiment of FIG. 12, a length of the package 10 along the longitudinal axis can be in a range of 7 mm to 11 mm, in a range of 7 mm to 10 mm, or in a range of 8 mm to 10 mm.

The molding material 32 can be applied over portions of the dies 13, 12, 28 and the substrate 15. In some embodiments, the molding material 32 can be disposed entirely around the package 10. In some other embodiments, the molding material 32 can be disposed partially around the package 10. For example, in the embodiment of FIGS. 12-13, a first portion of the molding material can be disposed over the first die 13, the second die 12, and the intervening twisted section 17 of the substrate 15. In some embodiments the molding material 32 can be disposed only over the twisted section 17. In some embodiments, the molding material 32 can be disposed over the twisted section 17 and one or more of the dies 13, 12, 28. Thus, the molding material 32 can be disposed over any portion of the package 10 so as to define or maintain the fixed non-parallel angle and/or protect the first die 13, the second die 12 and/or the third die 28.

Figure 14:
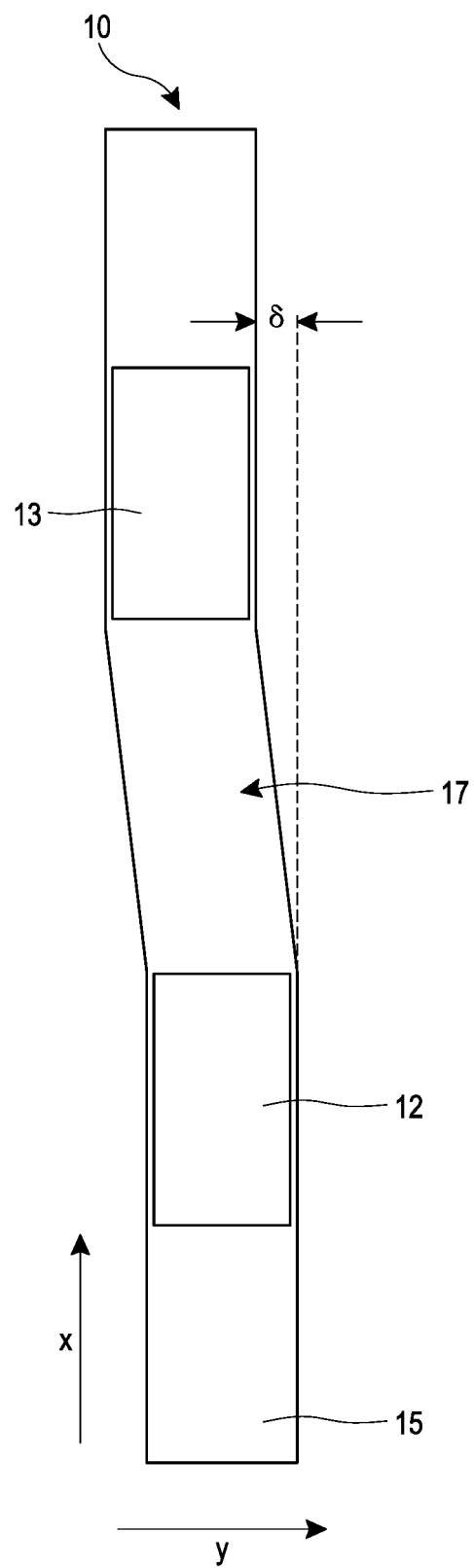
FIG. 14 is a schematic top-down plan view of the package showing the dies mounted in a common plane on a substrate, in a stage of manufacturing prior to twisting the substrate.
Figure 15:
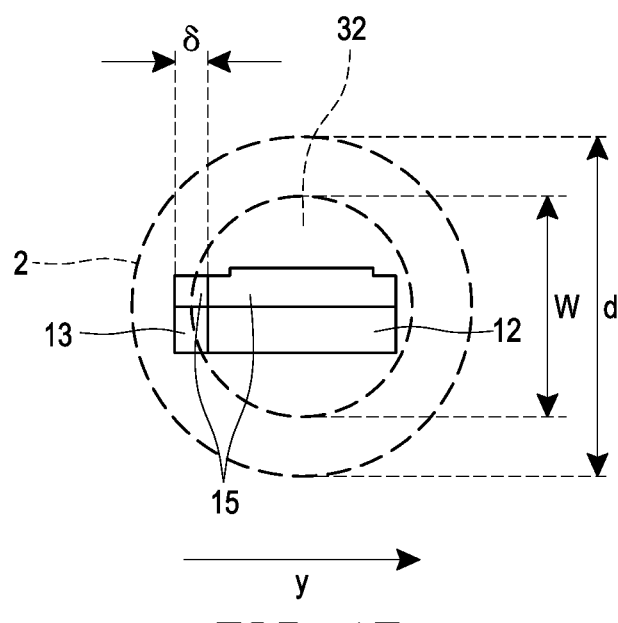
FIG. 15 is a schematic end view of the device package of FIG. 14, as viewed along the longitudinal axis of the package.

FIG. 14 is a schematic top-down plan view of the package 10 with an offset before forming the fixed non-parallel angle, e.g., before twisting the dies 13, 12 relative to one another. FIG. 15 is a schematic end view of the device package 10 of FIG. 14 overlaid within the lumen 11 of the body 2. In FIG. 15, the molding compound is omitted for ease of illustration. FIG. 15 therefore illustrates a schematic rendering of how, prior to twisting the substrate 15, the package 10 is wider than the lumen 11 of the elongate body 2 (e.g., the catheter). As shown in FIGS. 14 and 15, the substrate 15 is shifted or laterally offset at the twisted section 17 so as to make the integrated dies 12, 13 offset along a transverse axis y to create a lateral offset δ between the dies 13, 12 before twisting. The lateral offset δ between the dies 13, 12 allows the dies 13, 12 to fit within the diameter d of the elongate body 2 after twisting. Thus, the offset δ can be selected such that, after twisting the substrate 15 to define the twisted section 17, the dies 13, 12 and substrate 15 can fit within the diameter d of the elongate body 2, despite the fact that it could not fit prior to twisting. The offset δ can typically be determined by sizes of the substrate 15 and other components of the package 10 along the transverse axis, but other factors may affect the determination of the offset δ. The offset δ can be in a range of 10 microns to 200 microns, in a range of 20 microns to 150 microns, or in a range of 40 microns to 100 microns.

The package 10 can be manufactured by mounting the first and second integrated device dies 13, 12 on the substrate 15. The dies 13, 12 can be spaced apart from each other along the longitudinal axis x, and along the transverse axis x by an offset δ. The substrate 15 can be deformed (e.g., twisted) so as to angle the dies 13, 12 relative to one another about the longitudinal axis x by the fixed non-parallel angle (about 90° in some arrangements, e.g., in a range from 89° to 91°, or in a range from 89.5° to 90.5°). The molding material 32 can be applied to the package 10 to fix the fixed non-parallel angle (in the absence of a bracket assembly or another structure that fixes the angle) and/or to protect the dies 13, 12, 28 at a molding step.

The first and second integrated device dies 13, 12 can be electrically connected to the substrate 15. For example, the dies 13, 12 may be flip chip mounted to the substrate 15 by way of a plurality of solder balls. For another example, the dies 13, 12 can be wire bonded to the substrate 15 using conductive bonding wires. In some embodiments, the third die 28 can also be mounted on and electrically connected to the substrate 15. In some embodiments, the deforming step can include offsetting the substrate 15 in the transverse axis y, twisting the substrate 15, and/or adhering the substrate 15 to the bracket assembly 14.

Figure 16:
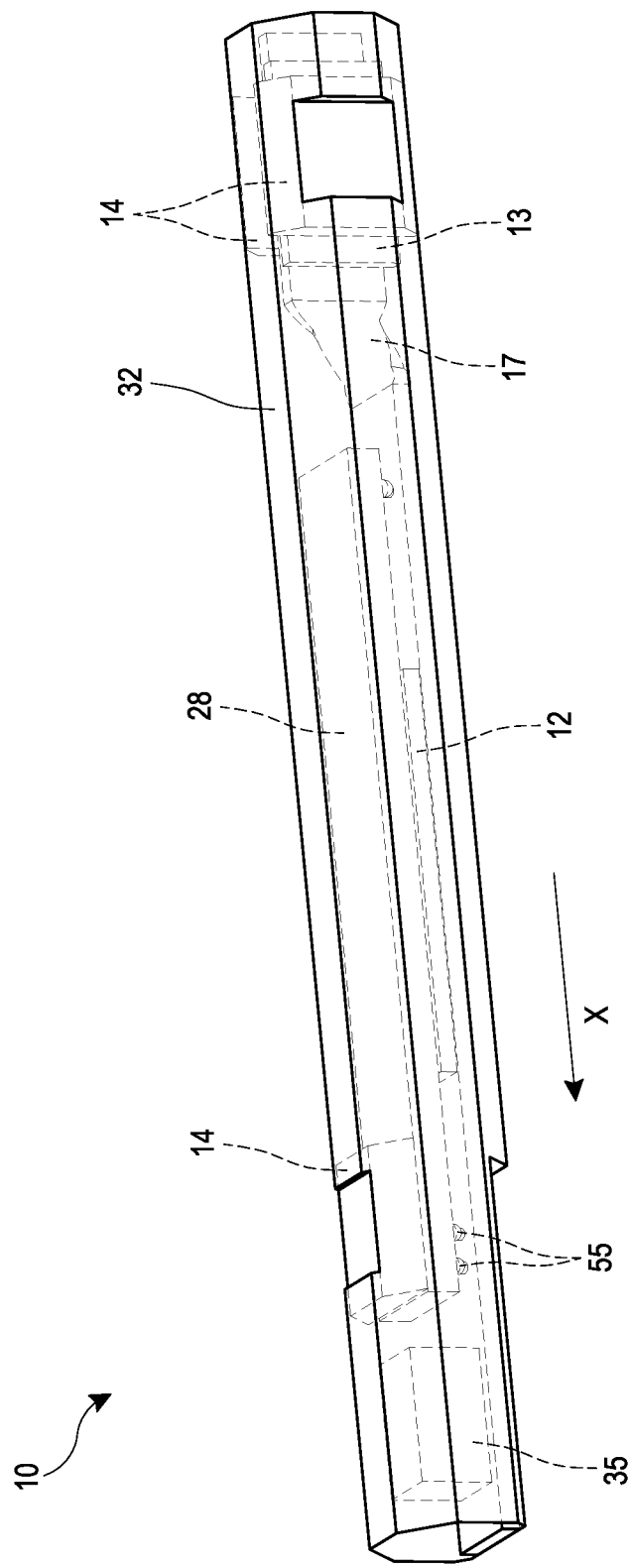
FIG. 16 is a schematic front perspective view of an integrated device package, according to another embodiment.

FIG. 16 is a schematic front perspective view of an integrated device package 10, according to another embodiment. In FIG. 16, as with the embodiments described above, the package 10 can include first and second integrated device dies 13, 12 (which may comprise motion sensor dies as explained above), a third integrated device die 28 (which can comprise a processor die or ASIC configured to process signals transduced by the dies 13, 12) with the dies 13, 12, 28 at least partially surrounded by a molding material 32. As with the embodiment of FIG. 12, the molding material 32 can be the structure that maintains the fixed non-parallel angle between the dies 13, 12. The package 10 of FIG. 16 is generally similar to the package 10 illustrated in FIG. 12. However, unlike the third integrated device die 28 of FIG. 12, the third integrated device die 28 of FIG. 16 can be stacked over the second die 12. Further, the embodiment shown in FIG. 16 includes a bracket assembly 14, although in other embodiments, the package 10 of FIG. 16 may not include any brackets or other structures that separately support or stiffen the dies 13, 12, 28. For example, as shown in FIG. 16, a first bracket 14a can be connected to the first die 13 and the opposite side of the portion of the substrate 15 to which the die 13 is mounted, such that the first die 13 and the substrate 15 are disposed between the first brackets.

In addition, as shown in FIG. 16, one or more passive components 35 (such as a capacitor) may be mounted to and electrically connected to the substrate 15 adjacent the second and third dies 12, 28. The passive component(s) 35 can be configured to smooth signals prior to or after processing by the third die 28. In various embodiments, it may be desirable to dimension the passive component 35 sufficiently small such that the entire sizing of the package 10 is not affected by the dimension of the passive component 35. For example, the dimension of the passive component 35 can be less than 0.3 mm along the transverse axis, less than 0.5 mm along the longitudinal axis and less than 0.3 mm in height.

The third integrated device die 28 (for example, a processor die or ASIC) can be electrically connected to the substrate by any suitable method, e.g., by way of solder balls 55). As shown in FIG. 16, for example, the solder balls 55 can provide vertical standoff of the third die 28 relative to the substrate 15, e.g., to provide clearance or a cavity sufficiently sized to receive the second die 12 between the third die 28 and the substrate 15. In some embodiments, the third die 28 can contact the second die 12, but in other embodiments, the third die 28 can be vertically spaced above the second die 12, e.g., the solder balls 55 can space the third die 28 above the second die 12 in some embodiments. In other embodiments, the third integrated device die 28 may be, for example, wire bonded to the substrate 15.

Stacking the third integrated device die 28 over the second integrated device die 12 can advantageously shorten the length of the package along the longitudinal axis x, as compared with the embodiments of FIG. 12, since the second and third dies 12, 28 can be positioned at about the same longitudinal position along the elongate body 2. In the illustrated embodiment of FIG. 12, a length of the package 10 along the longitudinal axis can be in a range of 3 mm to 6 mm, in a range of 3.5 mm to 5.5 mm, in a range of 3.5 mm to 5 mm, in a range of 4 mm to 5.5 mm, or in a range of 4 mm to 5 mm, e.g., about 4.5 mm in one embodiment.

Stacking the third integrated device die 28 over the second integrated device die 12 can also advantageously reduce a total length of traces embedded in the substrate 15 by making the substrate 15 more compact as compared with the embodiment of FIG. 12.

The bracket assembly 14 can be used for twisting the substrate 15, for protecting the dies 13, 12, 28, and/or for supporting the dies 13, 12, 28 and substrate 15 during molding. In the illustrated embodiment, the final package 10 can include the bracket assembly 14. In other embodiment, the bracket assembly 14 can be eliminated in a final product.

Figure 17:
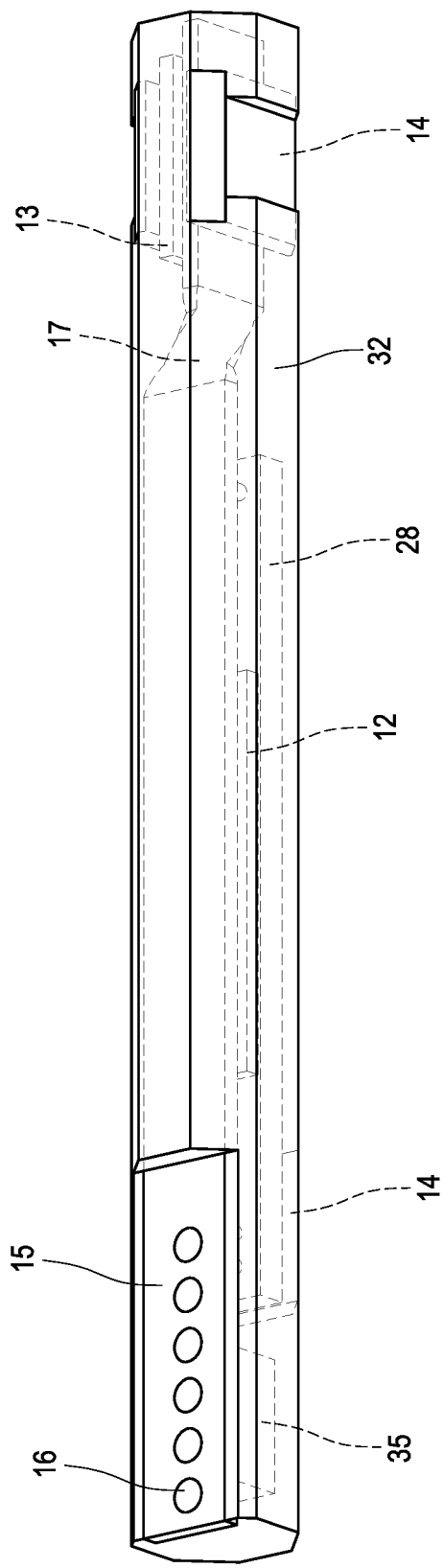
FIG. 17 is a schematic back perspective view of the integrated device package of FIG. 16.

FIG. 17 is a schematic back perspective view of the integrated device package 10 of FIG. 16. The package 10 as illustrated in FIG. 17 has conductive leads 16 on the substrate 15. The number of the conductive leads 16 shown is six, however, there can be any suitable number of conductive leads 16.

Figure 18:
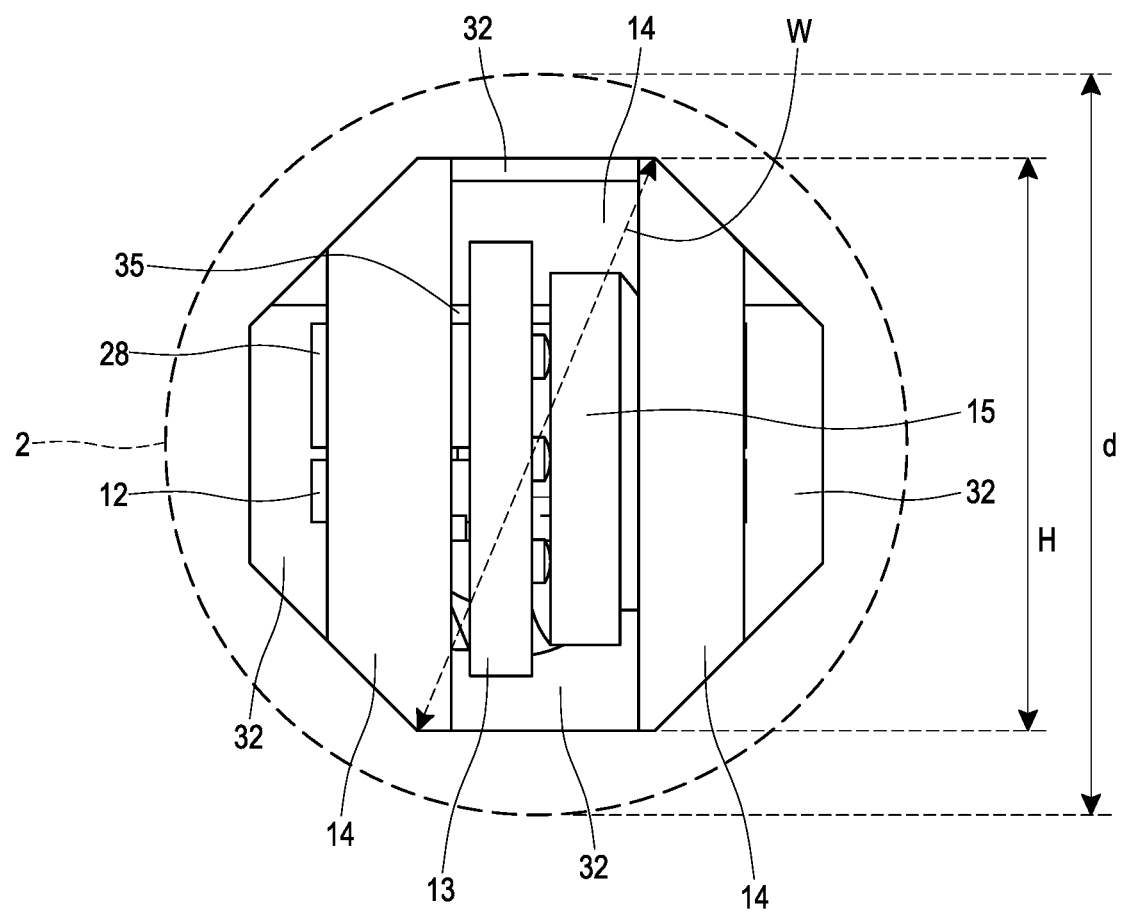
FIG. 18 is a schematic end view of the integrated device package of FIGS. 16 and 17, as viewed along the longitudinal axis of the package.

FIG. 18 is a schematic end view of the integrated device package 10 of FIGS. 16 and 17, as viewed along the longitudinal axis x of the package. As explained with respect to the embodiment shown in FIG. 6, the molding material 32 that surrounds the package 10 can have a height H (as measured from a flat surface of the octagonal shape to an opposing flat surface as shown in FIG. 18) along a transverse axis that is perpendicular to the longitudinal axis x. In some embodiments, the height H can be around 450 microns: The height H can be in a range of 300 microns to 600 microns, in a range of 300 microns to 550 microns, in a range of 350 microns to 550 microns, in a range of 350 microns to 500 microns, in a range of 400 microns to 550 microns, or in a range of 400 microns to 500 microns. In the embodiment shown in FIG. 18, portions of the molding material 32 (which may originally have a circular profile) can be trimmed to form an octagonal shape, which can beneficially reduce the overall lateral dimensions of the package 10 and to improve the fit of the package 10 within the elongate body 2. The width W for the embodiment illustrated in FIG. 18 can be generally similar to the width W for the embodiment illustrated in FIG. 6. In the embodiment illustrated in FIG. 18, the width W can be a dimension measured from a vertex to another vertex farthest from the vertex, e.g., the width W can define a major lateral or transverse dimension of the package 10.

Figure 19:
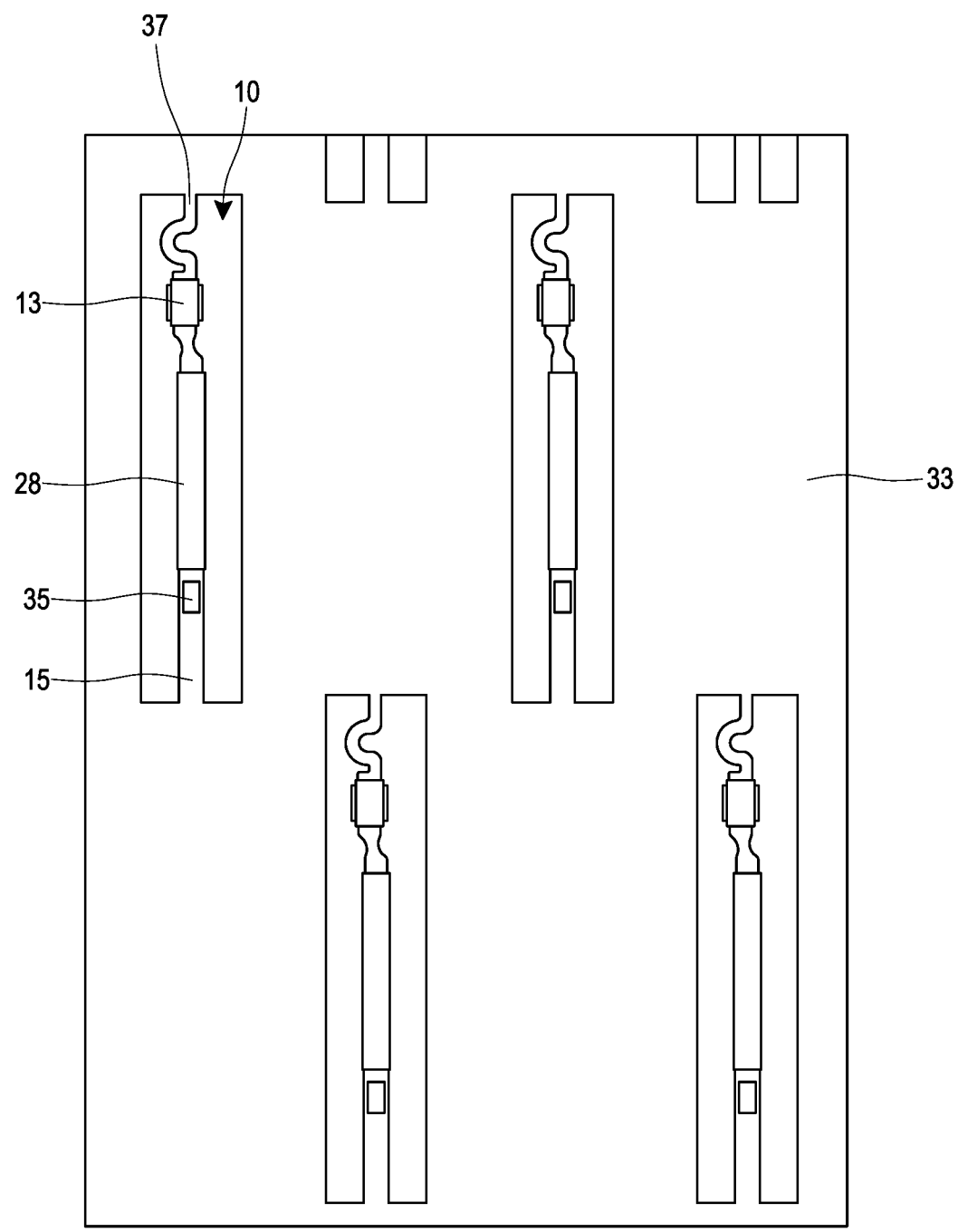
FIG. 19 is a top perspective view of the integrated device packages of FIGS. 16 and 17 coupled with a frame during a manufacturing process prior to forming a twisted section.

FIG. 19 is a top perspective view of the integrated device packages 10 of FIGS. 16 and 17 coupled with a frame 33 during a manufacturing process prior to forming the twisted section 17. In each package 10, the substrate 15 can have a winding 37 for easily twisting the first integrated device die 13 relative to the second and third integrated device die 12, 28. It should be understood that the winding 37 can be disposed at a different portion of the substrate 15 from what is illustrated in FIG. 19.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. An integrated device package comprising:
   a package substrate;
   a first integrated device die mounted to the package substrate;
   a second integrated device die mounted to the package substrate, the first integrated device die spaced from the second integrated device die on the package substrate along a longitudinal axis, the first and second integrated device dies angled relative to one another about the longitudinal axis by a fixed non-parallel angle in a transverse plane non-parallel to the longitudinal axis;
   a molding material at least partially disposed over the package substrate between the first and second integrated device dies to maintain the fixed non-parallel angle; and a bracket assembly extending along a longitudinal axis serving as a stiffener for the first and second integrated device dies.

2. The package of claim 1, wherein the package substrate comprises a twisted section disposed between the first and second integrated device dies, the molding material disposed over at least a portion of the twisted section.

3. The package of claim 1, wherein the package substrate comprises a flexible insulating sheet with embedded conductors.

4. The package of claim 1, wherein the first and second integrated device dies comprise sensor dies.

5. The package of claim 4, wherein the first and second integrated device dies comprise magnetoresistance sensors, the magnetoresistance sensors comprising at least one of anisotropic magnetoresistance (AMR) sensors, tunneling magnetoresistance (TMR) sensors, and giant magnetoresistance (GMR) sensors.

6. The package of claim 5, wherein the first integrated device die is configured to sense a position of the package along first and second orthogonal axes, and wherein the second integrated device die is configured to sense the position of the package along a third axis orthogonal to the first and second axes.

7. The package of claim 5, further comprising a third integrated device die mounted to the package substrate, the third integrated device die configured to process position data transduced by the first and second integrated device dies.

8. The package of claim 7, wherein the third integrated device die is an analog-to-digital converter (ADC).

9. The package of claim 7, wherein the third integrated device die is stacked over the second integrated device die.

10. The package of claim 1, wherein one or more of the first and second integrated device dies is flip chip mounted or wire bonded to the package substrate.

11. The package of claim 1, wherein a length of the integrated device package along the longitudinal axis is in a range of 3 mm to 15 mm, and the package has a width along a transverse axis that is perpendicular to the longitudinal axis, the width being in a range of 50 microns to 600 microns.

12. The package of claim 1, wherein the fixed non-parallel angle is formed by a twisted section of the package substrate, and the fixed non-parallel angle is in a range of 89° to 91°.

13. An integrated device package comprising:
a package substrate;
a first integrated device die mounted to the package substrate;
a second integrated device die mounted to the package substrate, the first integrated device die spaced from the second integrated device die on the package substrate along a longitudinal axis, the first and second integrated device dies angled relative to one another about the longitudinal axis by a fixed non-parallel angle in a transverse plane non-parallel to the longitudinal axis,
wherein the integrated device package has a width along a transverse axis that is perpendicular to the longitudinal axis, the width being in a range of 50 microns to 600 microns; and
a bracket assembly extending along a longitudinal axis and serving as a stiffener for the first and second integrated device dies.

14. The package of claim 13, further comprising a molding material that fixes the fixed non-parallel angle.

15. The package of claim 13, wherein the first and second integrated device dies comprise sensor dies.

* * * * *